US008859722B2

(12) United States Patent
Hoey et al.

(10) Patent No.: US 8,859,722 B2
(45) Date of Patent: *Oct. 14, 2014

(54) HEMOLYSIN AND ITS PROTEIN FRAGMENTS IN SERO-DETECTION OF ANAPLASMA PHAGOCYTOPHILUM

(75) Inventors: John G. Hoey, Framingham, MA (US); Denise P. Dimitrov, Hamilton, NJ (US); Lisa P. Huang, Princeton, NJ (US); Martin E. Adelson, East Windsor, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,624

(22) Filed: Jul. 30, 2012

(65) Prior Publication Data

US 2013/0189715 A1 Jul. 25, 2013

Related U.S. Application Data

(62) Division of application No. 12/658,537, filed on Feb. 9, 2010, now Pat. No. 8,257,938.

(60) Provisional application No. 61/208,876, filed on Feb. 27, 2009.

(51) Int. Cl.
*C07K 14/195* (2006.01)
*C07K 14/29* (2006.01)
*G01N 33/569* (2006.01)

(52) U.S. Cl.
CPC ............ *C07K 14/29* (2013.01); *G01N 2469/20* (2013.01); *G01N 33/56911* (2013.01); *C07K 14/195* (2013.01)
USPC .......................... 530/300; 530/324; 424/186.1

(58) Field of Classification Search
CPC ..................................... C07K 14/195
USPC ......................................... 530/300
See application file for complete search history.

(56) References Cited

U.S. PATENT DOCUMENTS

| 4,340,592 | A | * | 7/1982 | Adibi ............................. 514/5.5 |
| 5,380,656 | A | * | 1/1995 | Barrett et al. ................. 435/219 |
| 6,020,128 | A | * | 2/2000 | Steiner ......................... 435/6.15 |
| 7,807,810 | B2 | * | 10/2010 | Rikihisa et al. .............. 536/23.7 |
| 8,158,370 | B2 | * | 4/2012 | Liu et al. ........................ 435/7.1 |
| 8,257,938 | B2 | * | 9/2012 | Hoey et al. ................... 435/7.32 |
| 8,283,130 | B2 | * | 10/2012 | Hoey et al. ................... 435/7.32 |

(Continued)

OTHER PUBLICATIONS

Uniprot Accession No. Q2GLU3, pp. 1-5, Mar. 21, 2006.*

(Continued)

*Primary Examiner* — Albert Navarro
*Assistant Examiner* — Ginny Portner
(74) *Attorney, Agent, or Firm* — Siu K. Lo

(57) ABSTRACT

Disclosed is the cloning, expression and purification of a hemolysin protein and its protein fragments in *Anaplasma phagocytophilum*. The recombinant hemolysin and its protein fragments are useful in the ELISA detection of *anaplasma* pathogen. The use of same as a kit for ELISA is also disclosed.

16 Claims, 31 Drawing Sheets

Antigenicity Profile for *Anaplasma phagocytophilum* Hemolysin

(56) References Cited

U.S. PATENT DOCUMENTS

| | | | | |
|---|---|---|---|---|
| 8,323,907 | B2 * | 12/2012 | Hoey et al. | 435/7.1 |
| 8,338,190 | B2 * | 12/2012 | Hoey et al. | 436/518 |
| 8,389,678 | B2 * | 3/2013 | Hoey et al. | 530/300 |
| 2004/0214184 | A1 * | 10/2004 | Skubitz et al. | 435/6 |
| 2007/0264634 | A1 * | 11/2007 | Bock et al. | 435/6 |
| 2012/0207779 | A1 * | 8/2012 | Liu et al. | 424/190.1 |
| 2013/0064843 | A1 * | 3/2013 | Brusic et al. | 424/186.1 |
| 2013/0137595 | A1 * | 5/2013 | Zangar et al. | 506/9 |

OTHER PUBLICATIONS

Lin, M et al, Cellular Microbiology, 2003, vol. 5(11), pp. 809-820, Obligatory intracellular parasitism by *Ehrlichia chaffeensis* and *Anaplasma* phagocytophilum invoves caveolae and glycosylphosphatidylinositol-anchored proteins.*

Uniprot Acession No. Q5P9D4, pp. 1-5, Jan. 4, 2005.*

Hotopp, Julie C. Dunning et al, Comparative Genomics of Emerging Human Ehrlichiosis Agents, PLOS Genetics, vol. 2(2 e21), 2006, pp. 0208-0223.*

* cited by examiner

Antigenicity Profile for *Anaplasma phagocytophilum* Hemolysin

Hemolysin Amplicon for Expression in *E. coli* (Post-PCR Clean-up)

Figure 5

Hemolysin

Nucleotide Sequence (SEQ ID No. 16)

```
  1 atgggtgctg gagttttga agaagatgag ggaagtaacc tgactttctt
 51 caatcgctgg aaagcgcgtc tctactcttt tatctttaac aactttcctg
101 gatttaaaga ctttgcgaaa gatgcggtgt ttcgtagaaa catatttggc
151 ttcaattgtt tcaacataat gggtaatttg gtaagttttg atgattgctc
201 acttcaggaa ataatggtgc aaaggtcgga aattagggct tttgccatag
251 atgacagtga cttagttaat agtgtcctta aaagccaaca tacaagagtc
301 cctgtatata aagacaatct ggataatatt gtcgggttta ttcacattag
351 agatattctg atgaagggtg gttcagattt taatgtgaaa gacgttatac
401 gcgatgttat ttatgttcca cattctatga aggcggtcag cctatttgtt
451 aaaatgcagt cttctagagt tcacatggct attgtgcttg acgagtatgg
501 tagtactgat ggtcttgtaa caatggaaga tataatagaa cctatagtag
551 gtgatatcga atacgaaaac gatgagactg ctattcctga tattgtaaac
601 atttcagaca atacaattga ggtgaatgcc agagttttgg ttcgaacctt
651 ggagcgcact ttgggagtgg tgttaagaga ctcgtctgct gaagaagatt
701 atgacactgt agggggctt atttcgcta tggtaggcag ggtaccagtt
751 gtagatgagg ttttccaaca taaagtggt gcggtcttta caataaaaga
801 ggctgataat cgctgcatat atagggttat tattgatcta tcaggcgtga
851 ataggaatac tgcttgctga
```

Deduced Amino Acid Sequence (SEQ ID No. 17)

```
MGAGVFEEDEGSNLTFFNRWKARLYSFIFNNFPGFKDFAKDAVFRRNIFG  50
FNCFNIMGNLVSFDDCSLQEIMVQRSEIRAFAIDDSDLVNSVLKSQHTRV 100
PVYKDNLDNIVGFIHIRDILMKGGSDFNVKDVIRDVIYVPHSMKAVSLFV 150
KMQSSRVHMAIVLDEYGSTDGLVTMEDIIEPIVGDIEYENDETAIPDIVN 200
ISDNTIEVNARVLVRTLERTLGVVLRDSSAEEDYDTVGGLIFAMVGRVPV 250
VDEVFQHKSGAVFTIKEADNRCIYRVIIDLSGVNRNTAC*
```

Colony PCR of Hemolysin Transformants in NovaBlue *E. coli*:
(PCR-Amplified with Ek/LIC Primers)

Colony PCR of Hemolysin Transformants in BL21 E. coli for Expression:
(PCR-Amplified with vector-specific primers)

Nickel Column Purification of Recombinant Hemolysin (Urea denaturing conditions)

E1-E5: Elution pH 5.9
E6-E10: Elution pH 4.5

Sensitivity: 81.0%
Specificity: 57.1%

Hemolysin (Full-Length) IgG ELISA ROC Analysis

Hemolysin (Full-Length) IgM ELISA

Sensitivity: 60.0%
Specificity: 92.9%

Figure 17

Hemolysin Fragment 1

Nucleotide Sequence (SEQ ID NO. 18)

```
  1 atgggtgctg gagtttttga agaagatgag ggaagtaacc tgactttctt
 51 caatcgctgg aaagcgcgtc tctactcttt tatctttaac aactttcctg
101 gatttaaaga ctttgcgaaa gatgcggtgt ttcgtagaaa catatttggc
151 ttcaattgtt tcaacataat gggtaatttg gtaagttttg atgattgctc
201 acttcaggaa ataatggtgc aaaggtcgga aattagggct tttgccatag
251 atgacagtga cttagttaat agtgtcctta aaagccaaca tacaagagtc
```

Deduced Amino Acid Sequence (SEQ ID NO. 19)

```
MGAGVFEEDEGSNLTFFNRWKARLYSFIFNNFPGFKDFAKDAVFRRNIFG 50
FNCFNIMGNLVSFDDCSLQEIMVQRSEIRAFAIDDSDLVNSVLKSQHTRV* 100
```

Figure 18

Hemolysin Fragment 2

Nucleotide Sequence (SEQ ID NO. 20)

```
  1 agtgtcctta aaagccaaca tacaagagtc cctgtatata aagacaatct
 51 ggataatatt gtcgggttta ttcacattag agatattctg atgaagggtg
101 gttcagattt taatgtgaaa gacgttatac gcgatgttat ttatgttcca
151 cattctatga aggcggtcag cctatttgtt aaaatgcagt cttctagagt
201 tcacatggct attgtgcttg acgagtatgg tagtactgat ggtcttgtaa
251 caatggaaga tataatagaa cctatagtag gtgatatcga atacgaaaac
```

Deduced Amino Acid Sequence (SEQ ID NO. 21)

MKGGSDFNVKDVIRDVIYVPHSMKAVSLFVKMQSSRVHMAIVLDEYGSTD 50
GLVTMEDIIEPIVGDIEYEN*

Figure 19

Hemolysin Fragment 3

Nucleotide Sequence (SEQ ID NO. 22)

```
  1 gatgagactg ctattcctga tattgtaaac atttcagaca atacaattga
 51 ggtgaatgcc agagttttgg ttcgaacctt ggagcgcact ttgggagtgg
101 tgttaagaga ctcgtctgct gaagaagatt atgacactgt aggggggctt
151 attttcgcta tggtaggcag ggtaccagtt gtagatgagg ttttccaaca
201 taaaagtggt gcggtcttta caataaaaga ggctgataat cgctgcatat
251 atagggttat tattgatcta tcaggcgtga ataggaatac tgcttgctga
```

Deduced Amino Acid Sequence (SEQ ID NO. 23)

MVGRVPVVDEVFQHKSGAVFTIKEADNRCIYRVIIDLSGVNRNTAC*

Induction of Hemolysin Fragment 1

Nickel Column Purification of Hemolysin Fragment 1

Hemolysin Fragment-1 IgG ELISA ROC Analysis

Nickel Column Purification of Hemolysin Fragment 2 (from Inclusion Body Fraction)

Hemolysin Fragment-2 IgG ELISA ROC Analysis

Nickel Column Purification of Hemolysin Fragment 3 (from Soluble Fraction)

Hemolysin Fragment-3 IgG ELISA ROC Analysis

SEQUENCE LISTING

<160> NUMBER OF SEQ ID NOS: 23

<210> SEQ ID NO 1
<211> LENGTH: 34
<212> TYPE: DNA
<213> ORGANISM: Anaplasma Phagocytophilum
<220> FEATURE:
<223> OTHER INFORMATION: Primer

<400> SEQUENCE: 1
gacgacgaca agatgggtgc tggagttttt gaag         34

<210> SEQ ID NO 2
<211> LENGTH: 39
<212> TYPE: DNA
<213> ORGANISM: Anaplasma Phagocytophilum
<220> FEATURE:
<223> OTHER INFORMATION: Primer

<400> SEQUENCE: 2
gaggagaagc ccggttcagc aagcagtatt cctattcac         39

<210> SEQ ID NO 3
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 3
gacgacgaca agatggtgca gttttctttt gcc         33

<210> SEQ ID NO 4
<211> LENGTH: 37
<212> TYPE: DNA
<213> ORGANISM: Anaplasma Phagocytophilum
<220> FEATURE:
<223> OTHER INFORMATION: Primer

<400> SEQUENCE: 4
gaggagaagc ccggtctaga gctccaatcc ttttatc         37

<210> SEQ ID NO 5
<211> LENGTH: 34
<212> TYPE: DNA
<213> ORGANISM: Anaplasma Phagocytophilum
<220> FEATURE:
<223> OTHER INFORMATION: Primer

<400> SEQUENCE: 5
gacgacgaca agatgctaag gctcatggtg atgg         34

<210> SEQ ID NO 6
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 6
gaggagaagc ccggttcaaa aacgtattgt gcgacg         36

<210> SEQ ID NO 7
<211> LENGTH: 289
<212> TYPE: PRT
<213> ORGANISM: Anaplasma Phagocytophilum

<400> SEQUENCE: 7

```
Met Gly Ala Gly Val Phe Glu Glu Asp Glu Gly Ser Asn Leu Thr Phe
1               5                   10                  15

Phe Asn Arg Trp Lys Ala Arg Leu Tyr Ser Phe Ile Phe Asn Asn Phe
                20                  25                  30

Pro Gly Phe Lys Asp Phe Ala Lys Asp Ala Val Phe Arg Arg Asn Ile
            35                  40                  45

Phe Gly Phe Asn Cys Phe Asn Ile Met Gly Asn Leu Val Ser Phe Asp
        50                  55                  60

Asp Cys Ser Leu Gln Glu Ile Met Val Gln Arg Ser Glu Ile Arg Ala
65                  70                  75                  80

Phe Ala Ile Asp Asp Ser Asp Leu Val Asn Ser Val Leu Lys Ser Gln
                85                  90                  95

His Thr Arg Val Pro Val Tyr Lys Asp Asn Leu Asp Asn Ile Val Gly
            100                 105                 110

Phe Ile His Ile Arg Asp Ile Leu Met Lys Gly Gly Ser Asp Phe Asn
        115                 120                 125

Val Lys Asp Val Ile Arg Asp Val Ile Tyr Val Pro His Ser Met Lys
130                 135                 140

Ala Val Ser Leu Phe Val Lys Met Gln Ser Ser Arg Val His Met Ala
145                 150                 155                 160

Ile Val Leu Asp Glu Tyr Gly Ser Thr Asp Gly Leu Val Thr Met Glu
                165                 170                 175

Asp Ile Ile Glu Pro Ile Val Gly Asp Ile Glu Tyr Glu Asn Asp Glu
            180                 185                 190

Thr Ala Ile Pro Asp Ile Val Asn Ile Ser Asp Asn Thr Ile Glu Val
        195                 200                 205

Asn Ala Arg Val Leu Val Arg Thr Leu Glu Arg Thr Leu Gly Val Val
210                 215                 220

Leu Arg Asp Ser Ser Ala Glu Glu Asp Tyr Asp Thr Val Gly Gly Leu
225                 230                 235                 240

Ile Phe Ala Met Val Gly Arg Val Pro Val Val Asp Glu Val Phe Gln
                245                 250                 255

His Lys Ser Gly Ala Val Phe Thr Ile Lys Glu Ala Asp Asn Arg Cys
            260                 265                 270

Ile Tyr Arg Val Ile Ile Asp Leu Ser Gly Val Asn Arg Asn Thr Ala
        275                 280                 285

Cys
```

<210> SEQ ID NO 8
<211> LENGTH: 262
<212> TYPE: PRT
<213> ORGANISM: Anaplasma Phagocytophilum

<400> SEQUENCE: 8

```
Met Val Gln Phe Ser Leu Pro Lys Asn Ser Lys Ile Asn Pro Asn Gly
1               5                   10                  15

Lys Val Tyr Asn Ala Thr Glu Gly Ala Lys Arg Thr Gly Cys Phe Lys
                20                  25                  30

Ile Tyr Arg Trp Ser Pro Asp Gly Glu Asn Pro Arg Ile Asp Thr
            35                  40                  45

Tyr Tyr Ile Asp Leu Asp Lys Cys Gly Gln Met Val Leu Asp Ala Leu
        50                  55                  60
```

```
Ile Lys Val Lys Asn Glu Tyr Asp Ser Thr Leu Thr Phe Arg Arg Ser
 65                  70                  75                  80

Cys Arg Glu Gly Ile Cys Gly Ser Cys Ala Met Asn Ile Asp Gly Thr
                 85                  90                  95

Asn Thr Leu Ala Cys Thr Lys Tyr Ile Ser Asp Ile Lys Gly Asp Val
            100                 105                 110

Lys Ile Phe Pro Leu Pro His Met Asp Val Ile Lys Asp Leu Val Pro
        115                 120                 125

Asp Leu Ser Asn Phe Tyr Lys Gln Tyr Lys Ser Ile Ser Pro Trp Leu
    130                 135                 140

Lys Ser Asp Gly Ala Arg Ser Asp Arg Glu Glu His Leu Gln Ser Ile
145                 150                 155                 160

Glu Asp Arg Ser Lys Leu Asp Lys Val Tyr Asp Cys Ile Leu Cys Ala
                165                 170                 175

Cys Cys Ser Thr Ser Cys Pro Ser Tyr Trp Trp Asn Pro Asp Lys Tyr
            180                 185                 190

Leu Gly Pro Ala Ala Leu Leu Gln Val Tyr Arg Trp Leu Val Asp Ser
        195                 200                 205

Arg Asp Thr Ala Thr Glu Glu Arg Leu Ala Phe Leu Glu Asp Ala Phe
    210                 215                 220

Lys Leu Tyr Arg Cys His Thr Ile Met Asn Cys Thr Lys Thr Cys Pro
225                 230                 235                 240

Lys Asp Leu Asn Pro Ala Lys Ala Ile Ala Lys Ile Lys Gln Met Met
                245                 250                 255

Ile Lys Gly Leu Glu Leu
            260

<210> SEQ ID NO 9
<211> LENGTH: 335
<212> TYPE: PRT
<213> ORGANISM: Anaplasma Phagocytophilum

<400> SEQUENCE: 9

Met Leu Arg Leu Met Val Met Val Val Leu Gln Gly Ser Gly Arg Ala
 1               5                  10                  15

Gly Tyr Phe Tyr Val Gly Leu Asp Tyr Ser Pro Ala Phe Ser Lys Ile
                 20                  25                  30

Arg Asp Phe Ser Ile Arg Glu Ser Asn Gly Glu Thr Lys Ala Val Tyr
             35                  40                  45

Pro Tyr Leu Lys Asp Gly Lys Ser Val Lys Leu Glu Ser Asn Lys Phe
         50                  55                  60

Asp Trp Asn Thr Pro Asp Pro Arg Ile Gly Phe Lys Asp Asn Met Leu
 65                  70                  75                  80

Val Ala Met Glu Gly Ser Val Gly Tyr Gly Ile Gly Gly Ala Arg Val
                 85                  90                  95

Glu Leu Glu Ile Gly Tyr Glu Arg Phe Lys Thr Lys Gly Ile Arg Asp
            100                 105                 110

Ser Gly Ser Lys Glu Asp Glu Ala Asp Thr Val Tyr Leu Leu Ala Lys
        115                 120                 125

Glu Leu Ala Tyr Asp Val Val Thr Gly Gln Thr Asp Asn Leu Ala Ala
    130                 135                 140

Ala Leu Ala Lys Thr Ser Gly Lys Asp Phe Val Gln Phe Ala Lys Ala
145                 150                 155                 160

Val Val Val Ser His Pro Gly Ile Asp Lys Lys Val Cys Ala Thr Lys
                165                 170                 175
```

-continued

```
Ala Gln Ser Ser Gly Lys Tyr Gly Lys Tyr Ala Asp Lys Thr Gly Thr
        180                 185                 190

Lys Ser Ser Asp Asn Asn Thr Ser Leu Cys Ser Asp Gly Gly Ser
195         200                 205

His Ser Gly Ser Ser Asn Asn Ala Glu Val Phe Glu His Phe Ile Lys
        210                 215                 220

Lys Thr Leu Leu Glu Asn Gly Ser Lys Asn Trp Pro Thr Ser Thr Lys
225                 230                 235                 240

Asn Asp Gly Ala Pro Ser Asp Lys Asn Asp Asn Ala Asp Ala Val
                245                 250                 255

Ala Lys Asp Leu Thr Lys Leu Thr Ser Glu Lys Thr Ile Val Ala
        260                 265                 270

Gly Leu Leu Ala Lys Thr Ile Glu Gly Gly Glu Val Val Glu Ile Arg
        275                 280                 285

Ala Val Ser Ser Thr Ser Val Met Val Asn Ala Cys Tyr Asp Leu Leu
        290                 295                 300

Ser Glu Gly Leu Gly Val Val Pro Tyr Ala Cys Val Gly Leu Gly
305             310                 315                 320

Asn Phe Val Gly Val Val Asp Gly Ser Arg Arg Thr Ile Arg Phe
                325                 330                 335
```

<210> SEQ ID NO 10
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 10
gacgacgaca agatgatggg tgctggagtt tt                              32

<210> SEQ ID NO 11
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 11
gaggagaagc ccggttagac tcttgtatgt tg                              32

<210> SEQ ID NO 12
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 12
gacgacgaca agatgagtgt ccttaaaagc ca                              32

<210> SEQ ID NO 13
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 13
gaggagaagc ccggttagtt ttcgtattcg ata                             33

<210> SEQ ID NO 14
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 14
gacgacgaca agatggatga gactgctatt cc                              32

<210> SEQ ID NO 15
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 15
gaggagaagc ccggttatca gcaagcagta tt                              32

<210> SEQ ID NO 16
<211> LENGTH: 870
<212> TYPE: DNA
<213> ORGANISM: Anaplasma Phagocytophilum

<400> SEQUENCE: 16
atgggtgctg gagtttttga agaagatgag ggaagtaacc tgactttctt caatcgctgg    60
aaagcgcgtc tctactcttt tatctttaac aactttcctg gatttaaaga ctttgcgaaa   120
gatgcggtgt ttcgtagaaa catatttggc ttcaattgtt tcaacataat gggtaatttg   180
gtaagttttg atgattgctc acttcaggaa ataatggtgc aaaggtcgga aattagggct   240
tttgccatag atgacagtga cttagttaat agtgtcctta aaagccaaca tacaagagtc   300
cctgtatata aagacaatct ggataatatt gtcgggttta ttcacattag agatattctg   360
atgaagggtg gttcagattt taatgtgaaa gacgttatac gcgatgttat ttatgttcca   420
cattctatga aggcggtcag cctatttgtt aaaatgcagt cttctagagt tcacatggct   480
attgtgcttg acgagtatgg tagtactgat ggtcttgtaa caatggaaga tataatagaa   540
cctatagtag gtgatatcga atacgaaaac gatgagactg ctattcctga tattgtaaac   600
atttcagaca atacaattga ggtgaatgcc agagttttgg ttcgaacctt ggagcgcact   660
ttgggagtgg tgttaagaga ctcgtctgct gaagaagatt atgacactgt aggggggctt   720
attttcgcta tggtaggcag ggtaccagtt gtagatgagg ttttccaaca taaaagtggt   780
gcggtcttta caataaaaga ggctgataat cgctgcatat atagggttat tattgatcta   840
tcaggcgtga ataggaatac tgcttgctga                                    870

<210> SEQ ID NO 17
<211> LENGTH: 289
<212> TYPE: PRT
<213> ORGANISM: Anaplasma Phagocytophilum

<400> SEQUENCE: 17

Met Gly Ala Gly Val Phe Glu Glu Asp Glu Gly Ser Asn Leu Thr Phe
1 5 10 15

Phe Asn Arg Trp Lys Ala Arg Leu Tyr Ser Phe Ile Phe Asn Asn Phe
20 25 30

Pro Gly Phe Lys Asp Phe Ala Lys Asp Ala Val Phe Arg Arg Asn Ile
35 40 45

```
Phe Gly Phe Asn Cys Phe Asn Ile Met Gly Asn Leu Val Ser Phe Asp
    50                  55                  60
Asp Cys Ser Leu Gln Glu Ile Met Val Gln Arg Ser Glu Ile Arg Ala
 65                  70                  75                  80
Phe Ala Ile Asp Ser Asp Leu Val Asn Ser Val Leu Lys Ser Gln
                 85                  90                  95
His Thr Arg Val Pro Val Tyr Lys Asp Asn Leu Asp Asn Ile Val Gly
                100                 105                 110
Phe Ile His Ile Arg Asp Ile Leu Met Lys Gly Ser Asp Phe Asn
                115                 120                 125
Val Lys Asp Val Ile Arg Asp Val Ile Tyr Val Pro His Ser Met Lys
    130                 135                 140
Ala Val Ser Leu Phe Val Lys Met Gln Ser Ser Arg Val His Met Ala
145                 150                 155                 160
Ile Val Leu Asp Glu Tyr Gly Ser Thr Asp Gly Leu Val Thr Met Glu
                165                 170                 175
Asp Ile Ile Glu Pro Ile Val Gly Asp Ile Glu Tyr Glu Asn Asp Glu
                180                 185                 190
Thr Ala Ile Pro Asp Ile Val Asn Ile Ser Asp Asn Thr Ile Glu Val
                195                 200                 205
Asn Ala Arg Val Leu Val Arg Thr Leu Glu Arg Thr Leu Gly Val Val
    210                 215                 220
Leu Arg Asp Ser Ser Ala Glu Glu Asp Tyr Asp Thr Val Gly Gly Leu
225                 230                 235                 240
Ile Phe Ala Met Val Gly Arg Val Pro Val Val Asp Glu Val Phe Gln
                245                 250                 255
His Lys Ser Gly Ala Val Phe Thr Ile Lys Glu Ala Asp Asn Arg Cys
                260                 265                 270
Ile Tyr Arg Val Ile Ile Asp Leu Ser Gly Val Asn Arg Asn Thr Ala
                275                 280                 285
Cys

<210> SEQ ID NO 18
<211> LENGTH: 300
<212> TYPE: DNA
<213> ORGANISM: Anaplasma Phagocytophilum

<400> SEQUENCE: 18
atgggtgctg agttttttga agaagatgag ggaagtaacc tgactttctt caatcgctgg     60
aaagcgcgtc tctactcttt tatctttaac aacttttcctg gatttaaaga ctttgcgaaa    120
gatgcggtgt ttcgtagaaa catatttggc ttcaattgtt tcaacataat gggtaatttg    180
gtaagttttg atgattgctc acttcaggaa ataatggtgc aaaggtcgga aattagggct    240
tttgccatag atgacagtga cttagttaat agtgtcctta aaagccaaca tacaagagtc    300

<210> SEQ ID NO 19
<211> LENGTH: 100
<212> TYPE: PRT
<213> ORGANISM: Anaplasma Phagocytophilum

<400> SEQUENCE: 19

Met Gly Ala Gly Val Phe Glu Glu Asp Glu Gly Ser Asn Leu Thr Phe
 1               5                  10                  15
Phe Asn Arg Trp Lys Ala Arg Leu Tyr Ser Phe Ile Phe Asn Asn Phe
                20                  25                  30
```

```
Pro Gly Phe Lys Asp Phe Ala Lys Asp Ala Val Phe Arg Arg Asn Ile
            35                  40                  45

Phe Gly Phe Asn Cys Phe Asn Ile Met Gly Asn Leu Val Ser Phe Asp
 50                  55                  60

Asp Cys Ser Leu Gln Glu Ile Met Val Gln Arg Ser Glu Ile Arg Ala
 65                  70                  75                  80

Phe Ala Ile Asp Asp Ser Asp Leu Val Asn Ser Val Leu Lys Ser Gln
                 85                  90                  95

His Thr Arg Val
            100

<210> SEQ ID NO 20
<211> LENGTH: 300
<212> TYPE: DNA
<213> ORGANISM: Anaplasma Phagocytophilum

<400> SEQUENCE: 20
agtgtcctta aaagccaaca tacaagagtc cctgtatata aagacaatct ggataatatt     60
gtcgggttta ttcacattag agatattctg atgaaggtg gttcagattt taatgtgaaa    120
gacgttatac gcgatgttat ttatgttcca cattctatga aggcggtcag cctatttgtt    180
aaaatgcagt cttctagagt tcacatggct attgtgcttg acgagtatgg tagtactgat    240
ggtcttgtaa caatggaaga tataatagaa cctatagtag gtgatatcga atacgaaaac    300

<210> SEQ ID NO 21
<211> LENGTH: 70
<212> TYPE: PRT
<213> ORGANISM: Anaplasma Phagocytophilum

<400> SEQUENCE: 21

Met Lys Gly Gly Ser Asp Phe Asn Val Lys Asp Val Ile Arg Asp Val
  1               5                  10                  15

Ile Tyr Val Pro His Ser Met Lys Ala Val Ser Leu Phe Val Lys Met
                 20                  25                  30

Gln Ser Ser Arg Val His Met Ala Ile Val Leu Asp Glu Tyr Gly Ser
             35                  40                  45

Thr Asp Gly Leu Val Thr Met Glu Asp Ile Ile Glu Pro Ile Val Gly
 50                  55                  60

Asp Ile Glu Tyr Glu Asn
 65                  70

<210> SEQ ID NO 22
<211> LENGTH: 300
<212> TYPE: DNA
<213> ORGANISM: Anaplasma Phagocytophilum

<400> SEQUENCE: 22
gatgagactg ctattcctga tattgtaaac atttcagaca atacaattga ggtgaatgcc     60
agagttttgg ttcgaacctt ggagcgcact ttgggagtgg tgttaagaga ctcgtctgct    120
gaagaagatt atgacactgt agggggggctt attttcgcta tggtaggcag ggtaccagtt    180
gtagatgagg ttttccaaca taaaagtggt gcggtcttta caataaaaga ggctgataat    240
cgctgcatat ataggggttat tattgatcta tcaggcgtga ataggaatac tgcttgctga    300

<210> SEQ ID NO 23
<211> LENGTH: 46
<212> TYPE: PRT
<213> ORGANISM: Anaplasma Phagocytophilum
```

```
<400> SEQUENCE: 23

Met Val Gly Arg Val Pro Val Val Asp Glu Val Phe Gln His Lys Ser
1               5                   10                  15

Gly Ala Val Phe Thr Ile Lys Glu Ala Asp Asn Arg Cys Ile Tyr Arg
            20                  25                  30

Val Ile Ile Asp Leu Ser Gly Val Asn Arg Asn Thr Ala Cys
            35                  40                  45
```

HEMOLYSIN AND ITS PROTEIN FRAGMENTS IN SERO-DETECTION OF ANAPLASMA PHAGOCYTOPHILUM

CROSS-REFERENCE TO RELATED APPLICATIONS

This application is a division of U.S. application Ser. No. 12/658,537 filed Feb. 9, 2010, which claims the benefit under 35 U.S.C. §119(e) to U.S. Provisional Applications No. 61/208,876 filed Feb. 27, 2009, the contents of which are incorporated by reference herein in their entirety.

FIELD OF THE INVENTION

The present invention generally relates to the field of diagnostic assays for the detection of infectious agents in an animal, including humans. Particular embodiments disclosed herein encompass hemolysin and protein fragments thereof that are useful in the sero-detection of *Anaplasma phagocytophilum*.

BACKGROUND OF THE INVENTION

*Anaplasma phagocytophilum* is a tick-borne pathogen responsible for granulocytic anaplasmosis in humans (Bakken J. S., et al.: Human granulocytic ehrlichiosis in the upper Midwest United States. A new species emerging? *JAMA* 272: 212-218, 1994). There has been a steady rise in cases of *anaplasma* infections, alone or through co-infection with other tick-borne pathogens (Varde S., et al.: Prevalence of tick-borne pathogens in *Ixodes scapularis* in a rural New Jersey County. *Emerg. Infect. Dis.* 4: 97-99, 1998). Left unchecked, *anaplasma* infection can be a potentially fatal disease resulting from the targeting and replication of Ap within human neutrophils (Bakken J. S. et al.: *JAMA* 272: 212-218, 1994). *Anaplasma phagocytophilum* infection thus emerges as a significant healthcare concern.

Detection of *anaplasma* infection is crucial. Ideally, a diagnostic assay should be capable of detecting *anaplasma* infection at its earliest stages, when antibiotic treatment is most effective and beneficial. Traditional detection methods for *anaplasma* infection includes: (i) microscopic identification of morulae in granulocytes, (ii) PCR analysis using whole blood, (iii) isolation of the *anaplasma* bacterium from whole blood, and (iv) serological tests, particularly indirect immunofluorescence assay (IFA). Microscopic examination is tedious and prone to sampling error. PCR test is sensitive in detecting the tick-borne pathogen during the period of time when the pathogen is present in the blood of infected patients. IFA is most commonly used (Park, J., et al.: Detection of antibodies to *Anaplasma phagocytophilum* and *Ehrlichia chaffeensis* antigens in sera of Korean patients by western immunoblotting and indirect immunofluorescence assays. *Clinical and Diagnostic Laboratory Immunology* 10(6): 1059-1064, 2003), but this test often gives false positive results. Such results can be attributed in part to the use of whole-cell antigens because such proteins may be shared with other bacteria (Magnarelli, L. A., et al.: Use of recombinant antigens of *Borrelia burgdorferi* and *Anaplasma phagocytophilum* in enzyme-linked immunosorbent assays to detect antibodies in white-tailed deer. *J. Wildlife Dis.* 40(2): 249-258, 2004). When clinical symptoms are manifested or high and stable antibody titers to *Anaplasma phagocytophilum* are found in patient blood, it reaches a late infection stage and bypass the window of antibiotic treatment.

So far, there are only a few surface proteins on *anaplasma* pathogen that are used in diagnostic assay for immuno-responses (i.e., IgG and IgM responses). It is generally believed that outer membrane proteins in pathogens are target for eliciting an immuno-response because they may be the first to be exposed to immune cells of a host. Regarding the *Anaplasma phagocytophilum* species, U.S. Pat. No. 6,964,855 discloses the use of an outer membrane protein and its fragments in a detection assay. U.S. Pat. No. 7,304,139 discloses a major surface protein 5 (MSP5) and its use in a diagnostic test. The '139 patent discloses a few patient's reactivity towards MSP5 and it lacks any data relating sensitivity and specificity, let alone any IgG/IgM distinction. Zhi et al. discloses cloning and expression of an outer membrane protein of 44 kDa and its use in a Western immunoblot assay (*J. Clinical Microbiology* 36(6): 1666-1673, 1998). Both MSP5 and p44 are outer membrane proteins in *Anaplasma phagocytophilum*. To the best knowledge of the inventors, there has been no report on using any intracellular protein as an antigenic protein, let alone its use in ELISA detection for *Anaplasma phagocytophilum*.

There is a continuing need in the discovery of a novel antigen present in *Anaplasma phagocytophilum* that may be useful in sero-detection of this pathogen. The present invention cures all the above-mentioned defects and provides a useful detection assay for *Anaplasma phagocytophilum* infection. Disclosed herein are the first cloning, expression, purification, and use of a recombinant hemolysin protein and its protein fragments. Particular embodiments include the development of a diagnostic ELISA test useful for detecting IgM/IgG antibody responses to *Anaplasma phagocytophilum*. The present assay represents the first demonstration of hemolysin as a good antigen for detecting *Anaplasma phagocytophilum*.

SUMMARY OF THE INVENTION

The present invention provides polypeptides of *anaplasma* hemolysin and its protein fragments thereof that are useful in the detection of *Anaplasma phagocytophilum*. Specifically, the present invention provides recombinant hemolysin and polypeptide fragments and methods of using these polypeptides in the detection of infections with *Anaplasma phagocytophilum*, which can be useful in the diagnosis of human granulocytic anaplasmosis.

In one aspect, the present invention provides an isolated polypeptide having an amino acid sequence selected from the group consisting of SEQ ID NO: 17, SEQ ID NO: 19, SEQ ID NO: 21 and SEQ ID NO: 23. Preferably, the isolated polypeptide hemolysin has an amino acid sequence set forth in SEQ ID NO: 16. Preferably, the recombinant hemolysin protein fragments having an amino acid sequence set forth in SEQ ID NO: 19, SEQ ID NO: 21 or SEQ ID NO: 23.

In another aspect, the present invention provides an isolated polynucleotide with nucleotide sequence set forth in SEQ ID NO: 0.16, SEQ ID NO: 18, SEQ ID NO: 20 or SEQ ID NO: 22.

In one aspect, the present invention provides a vector comprising the isolated polynucleotide of hemolysin or its protein fragments thereof. The vector may be pET. The vector may further comprise a promoter of DNA transcription operably linked to the isolated polynucleotides of interest. The vector may further comprise a promoter of DNA transcription operably linked to the isolated isolated polynucleotides of interest. The vector may be pET, pENTR, or pCR® 8/GW/TOPO®. The promoter may be a lac promoter, trp promoter or tac promoter.

In one aspect, the present invention provides a host cell comprising the vector. The host cell may be E. coli and the E. coli may include NovaBlue K12 strain or BL21 (DE3).

In one aspect, the present invention provides a method of producing an isolated polypeptide of hemolysin having an amino acid set forth in SEQ ID NO: 17, SEQ ID NO: 19, SEQ ID NO: 21, or SEQ ID NO: 23. The method comprises the steps of: (i) introducing an isolated hemolysin gene into a host cell, said isolated hemolysin gene is selected from the group consisting of SEQ ID NO: 16, SEQ ID NO: 18, SEQ ID NO: 20 and SEQ ID NO: 22; (ii) growing the host cell in a culture under suitable conditions to permit production of said isolated polypeptide; and (iii) isolating the isolated polypeptide of hemolysin.

In one aspect, the present invention provides a method of detecting the presence of an antibody against *Anaplasma phagocytophilum* in a biological sample of a mammal, comprising: (i) immobilizing an isolated polypeptide of hemolysin onto a surface, said isolated polypeptide having an amino acid sequences selected from the group consisting of SEQ ID NO: 17, SEQ ID NO: 19, SEQ ID NO: 21 and SEQ ID NO: 23, (ii) contacting the isolated polypeptide with a patient's biological sample, under conditions that allow formation of an antibody-antigen complex between the immobilized polypeptide and an antibody against *Anaplasma phagocytophilum*; and (iii) detecting the formation of the antibody-antigen complex; the detected antibody-antigen complex is indicative of the presence of said antibody against *Anaplasma phagocytophilum* in the biological sample. Preferably, the mammal is a human. ELISA test employs an IgG or IgM assay. Preferably, the ELISA has a sensitivity of at least >70%, and a specificity of at least >70%.

In another aspect, the present invention provides a method of diagnosing an infection of *Anaplasma phagocytophilum* in a mammal, comprising the steps of: (i) obtaining a biological sample from a mammal suspected of having an *Anaplasma phagocytophilum* infection; (ii) immobilizing an isolated polypeptide of hemolysin onto a surface, said isolated polypeptide having an amino acid sequences selected from the group consisting of SEQ ID NO: 17, SEQ ID NO: 19, SEQ ID NO: 21 and SEQ ID NO: 23; (iii) contacting the immobilized polypeptide with the biological sample, under conditions that allow formation of an antibody-antigen complex; and (iv) detecting said antibody-antigen complex. The detected antibody-antigen complex is indicative of the presence of said antibody against *Anaplasma phagocytophilum* in the biological sample. Preferably, the biological sample is whole blood, and the antibody is IgG or IgM.

In yet another aspect, the present invention provides an article of manufacture comprising a packaging material; and the isolated polypeptides of hemolysin. The article of manufacture may further comprise an instruction for detecting the presence of antibody against *Anaplasma phagocytophilum*.

BRIEF DESCRIPTION OF THE DRAWINGS

FIG. 5 depicts the Nucleotide Sequence for Hemolysin Gene in *Anaplasma phagocytophilum* (accession #YP 504658, SEQ ID NO:16), and the Deduced Amino Acid Sequence of Hemolysin Protein (SEQ ID NO:17).

FIG. 17 depicts the Nucleotide Sequence for Hemolysin Fragment 1 (SEQ ID NO: 18), and the Deduced Amino Acid Sequence of Hemolysin Fragment 1 (SEQ ID NO: 19).

FIG. 18 depicts the Nucleotide Sequence for Hemolysin Fragment 2 (SEQ ID NO: 20), and the Deduced Amino Acid Sequence of Hemolysin Fragment 2 (SEQ ID NO: 21).

FIG. 19 depicts the Nucleotide Sequence for Hemolysin Fragment 3 (SEQ ID NO: 22), and the Deduced Amino acid Sequence of Hemolysin Fragment 3 (SEQ ID NO: 23).

DETAILED DESCRIPTION OF THE INVENTION

Figure 1:
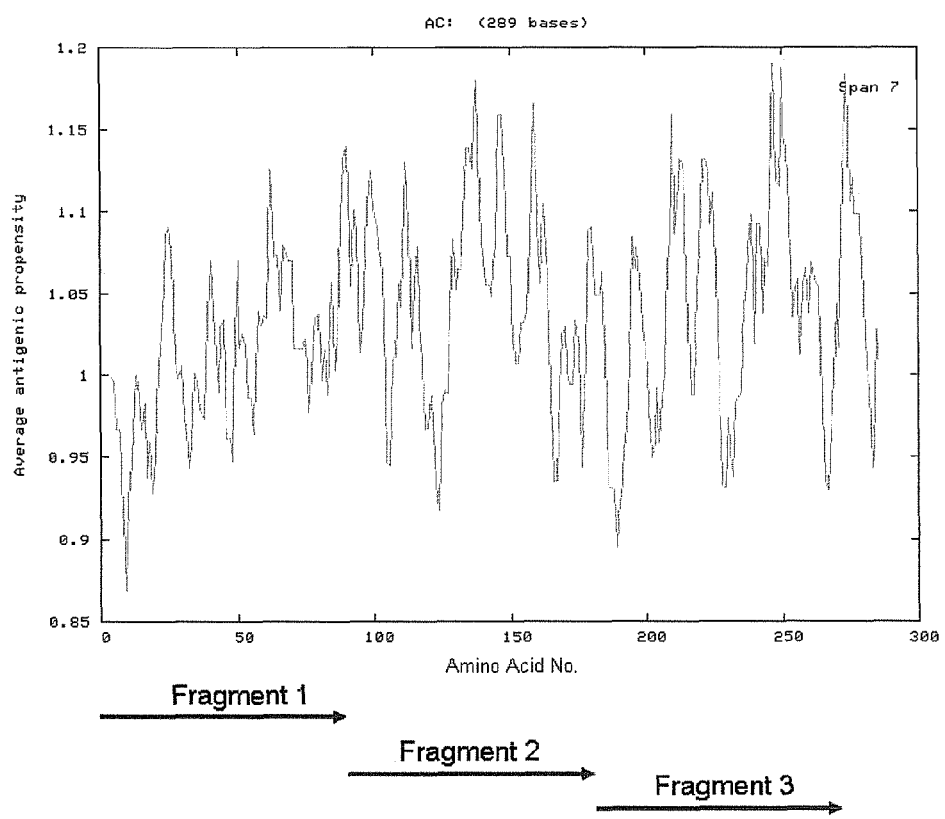
FIG. 1 depicts the Antigenicity Plot for Hemolysin Determined Using the Online Bioinformatics Tool.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, "hemolysin" refers to a polypeptide having an amino acid sequence as set forth in SEQ ID NO: 17 (NCBI Accession No. YP 504658). The polypeptide represents the putative hemolysin protein present in *Anaplasma phagocytophilum* strain HZ. The hemolysin polypeptide is shown by the present inventors to bind to antibodies that are present in *Anaplasma* patients' sera in an ELISA assay.

As used herein, "hemolysin fragment" refers to a fragment of the hemolysin polypeptide. The term "hemolysin fragment" is intended to include at least the three polypeptide fragments enclosed in this application (namely, fragment 1, fragment 2, and fragment 3). The amino acid sequences of these hemolysin fragments are set forth as below: hemolysin fragment 1 having amino acid as set forth in SEQ ID no. 19, hemolysin fragment 2 having amino acid as set forth in SEQ ID no. 21, and fragment 3 having amino acid as set forth in SEQ ID no. 23. These hemolysin fragments are shown herein capable of binding to antibodies that are present in *Anaplasma* patients' sera in an ELISA assay.

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Anaplasma phagocytophilum*. "IFA sero-negative sera from a patient" refers to sera (obtained from a patient) that exhibit negligible immunofluorescence staining towards cells that have been infected with *Anaplasma phagocytophilum*.

As used herein, the terms "polypeptide," "peptide," or "protein" are used interchangeably.

As used herein, the term "recombinant polypeptide" refers to a polypeptide that is recombinantly expressed by a host cell via the use of a vector that has been modified by the introduction of a heterologous nucleic acid. For purposes of the present invention, these polypeptides are intended to encompass some polypeptide variations insofar as they retain the ability to bind to antibodies present in *Anaplasma* infected patients in an ELISA assay with comparable sensitivity and specificity. One of an ordinary skill in the art would appreciate that the polypeptide variations may include (i) conservative substitutions, (ii) substitution, (iii) addition, and (iv) deletion of amino acids. It would be further appreciated that a polypeptide variant having a sufficiently high % amino acid sequence identity (e.g., >95%), when exhibited similar antibody binding activity as to the parent polypeptide, is encompassed by the present invention.

As used herein, the term "% amino acid sequence identity" is defined as the percentage of amino acid residues that are identical to the amino acid residues in the hemolysin polypeptide. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, blood serum, etc), cerebrospinal fluid, synovial fluid, and the like from a mammal such as a human or domestic animal. Extraction of nucleic acid from a biological sample is known to one of ordinary skill in the art.

As used herein, the term "ROC" refers to Receiver Operating Characteristics Analysis. ROC analysis is a standard statistical tool for evaluation of clinical tests. ROC accesses the performance of the system in terms of "Sensitivity" and "1-Specificity" for each observed value of the discriminator variable assumed as decision threshold (i.e., cutoff value to differentiate between two groups of response). For ELISA, the cutoff value can be shifted over a range of observed values (i.e., $OD_{450}$ nm reading), and Sensitivity and 1-Specificity can be established for each of these values. The optimal pair of Sensitivity and Specificity is the point with the greatest distance in a Northwest direction.

The present invention provides recombinant and synthetic polypeptides that, when assayed in an ELISA assay, react to IFA sero-positive sera and do not react to IFA sero-negative sera from a patient infected with *Anaplasma phagocytophilum*.

Recombinant Polypeptides of Hemolysin

The present invention specifically contemplates expression and preparation of recombinant and synthetic polypeptides, characterized by being capable of binding to antibodies present in IFA positive patient sera. In one embodiment, the present invention thus comprises the isolated nucleic acid having the nucleotide sequence set forth in FIG. 5 (SEQ ID NO: 16). The recombinant proteins of hemolysin expressed by the nucleic acids described herein encompasses the protein set forth in FIG. 5 (SEQ ID NO: 17). The recombinant hemolysin protein described herein possesses the ability to bind to antibodies present in IFA positive sera (and not IFA negative sera).

In another embodiment, the present invention thus comprises the isolated nucleic acid having the nucleotide sequence set forth in FIG. 17 (SEQ ID NO: 18). The recombinant proteins expressed by the nucleic acids described herein encompass those proteins set forth in FIG. 17 (SEQ ID NO: 19). The recombinant proteins of hemolysin described herein possess the ability to bind to antibodies present in IFA positive sera (and not IFA negative sera). The recombinant hemolysin protein possesses the ability to react to IFA-positive sera.

In one embodiment, the present invention provides a recombinant polypeptide containing an amino acid sequence as set forth in SEQ ID NO: 21. In another embodiment, the present provides a recombinant polypeptide containing an amino acid sequence set forth in SEQ ID NO: 23.

It is understood that these recombinant polypeptides encompass variants. One type of variants includes modification of amino acids of recombinant polypeptides; such as, for example, substitution, deletion, or addition of amino acids. The present invention is intended to encompass the polypeptide variants of hemolysin that retain the antibody binding ability towards IFA sero-positive sera and do not react to IFA sero-negative sera from *Anaplasma* infected patients. One of ordinary skill in the art would recognize that conservative amino acid substitutions may include simply substituting glutamic acid with aspartic acid; substituting isoleucine with leucine; substituting glycine or valine, or any divergent amino acid, with alanine, substituting arginine or lysine with histidine, and substituting tyrosine and/or phenylalanine with tryptophan. In another embodiment, addition and deletion of single amino acid may be employed. It is also appreciated by one of ordinary skill in the art that a few amino acids can be included or deleted from each or both ends, or from the interior of the polypeptide without significantly altering the peptide's ability to bind antibody (i.e., maintain high sensitivity and specificity (>70%), when tested in an ELISA assay.

Recombinant Expression of Hemolysin Polypeptides: Vectors and Hosts

Transcriptional and translational control sequences are DNA regulatory sequences, such as promoters, enhancers, terminators, and the like, that provide for the expression of a coding sequence in a host cell.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In one embodiment, the present invention provides the expression of the DNA sequences disclosed herein. As is well known in the art, DNA sequences may be recombinantly expressed by operatively linking the sequences to an expression control sequence in an appropriate expression vector; and expressing that linked vector via transformation in an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pET, pENTR, and pCR® 8/GW/TOPO® and the like. The promoter contains lac promoter, trp promoter and tac promoter.

In one embodiment, a host cell contains the vector comprising the polynucleotides of the present invention. Exemplary host cell includes *E. coli*. Various *E. coli* strains include, for example, NovaBlue strain, BL21 (DE3), or BL21 pLysS (DE3).

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors, a person skilled in the art will be able to construct a variety of vector/expression control sequence/host combinations that will express the DNA sequences of this invention on fermentation or in large-scale animal culture.

For recombinant expression of the various proteins used in this application, genes encoding the various proteins of interest can be conveniently inserted into a cloning vector and the vector containing the gene of interest is transfected or transformed into a suitable host cell for protein expression. Various publicly available vectors may be used. For example, vectors may include a plasmid, cosmid, viral particle, or phage. Examples of vectors included pET30, pENTR, pCR8/GW/TOPO and the like. Vector components generally include, but are not limited to, one or more of a signal sequence, an origin of replication, a marker gene, an enhancer element, a promoter, and a transcription termination sequence. Construction of suitable vectors containing one or more of these components as well as the gene of interest employs standard ligation techniques which are known to the skilled artisan.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

Examples of suitable selectable markers for mammalian cells include those that enable the identification of cells competent to take up the antigen-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci.* USA, 77:4216 (1980). A suitable selection gene for use in yeast is the trp1 gene present in the yeast plasmid YRp7 (Stinchcomb et al., *Nature*, 282:39 (1979). The trp1 gene provides a selection marker for a mutant strain of yeast lacking the ability to grow in tryptophan, for example, ATCC No. 44076 or PEP4-1 (Jones, *Genetics*, 85:12 (1977)).

A number of promoters can be used in order to enhance the expression of the gene of interest. In one embodiment, a promoter can be employed which will direct expression of a polynucleotide of the present invention in *E. coli*. Other equivalent transcription promoters from various sources are known to those of skill in the art. Exemplary promoters include the β-lactamase and lactose promoter systems (Chang et al., Nature, 275:615 (1978)), alkaline phosphatase, a tryptophan (tip) promoter system (Goeddel, *Nucleic Acids Res.,* 8:4057 (1980)), and the like.

A promoter may be operably linked to the protein-encoding nucleic acid sequence to direct mRNA synthesis. Promoters recognized by a variety of potential host cells are well known. For example, promoters for use in bacterial systems also will contain a Shine-Dalgarno (S.D.) sequence operably linked to the DNA encoding the protein of interest.

Transcription of a DNA encoding the antigen by higher eukaryotes may be increased by inserting an enhancer sequence into the vector. Enhancers are cis-acting elements of DNA, usually about from 10 to 300 bp, that can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding *Anaplasma phagocytophilum* antigen.

The nucleic acid (e.g., genomic DNA) encoding recombinant *Anaplasma phagocytophilum* antigen of the present invention may be inserted into a replicable vector for cloning (amplification of the DNA) or for expression. For example, full-length hemolysin protein (SEQ ID No. 16) may be inserted into a replicable vector for cloning and for expression of full-length virB9 protein or fragments thereof. The appropriate nucleic acid sequence may be inserted into the vector by a variety of procedures. In general, DNA is inserted into an appropriate restriction endonuclease site(s) using techniques known in the art.

Host cells are transfected or transformed with expression or cloning vectors described herein for antigen production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*. These examples are illustrative rather than limiting.

Methods of eukaryotic cell transfection and prokaryotic cell transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology,* 52:456-457 (1978) can be employed. Transformations into yeast are typically carried out according to the method of Van Solingen et al., *J. Bact.,* 130:946 (1977). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, See Keown et al., Methods in Enzymology, 185:527-537 (1990). The particular selection of host/cloning vehicle combination may be made by those of skill in the art after due consideration of the principles set forth without departing from the scope of this invention (See, e.g., Sambrook et al., *Molecular Cloning, A Laboratory Manual* $2^{nd}$ edition, 1989, Cold Spring Harbor Press, NY).

The antigen may be recombinantly produced as a fusion polypeptide with a heterologous polypeptide. The heterologous polypeptide may serve as a signal sequence or other polypeptide having a specific cleavage site at the N-terminus of the mature protein or polypeptide. In general, the signal sequence may be a component of the vector, or it may be a part of the antigen-encoding DNA that is inserted into the vector. In mammalian cell expression, mammalian signal sequences may be used to direct secretion of the protein, such as signal sequences from secreted polypeptides of the same or related species, as well as viral secretory leaders. An overview of expression of recombinant proteins is found in *Methods of Enzymology v.* 185, Goeddel, D. V. ed. Academic Press (1990).

Recombinant gene expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Recombinant gene expression, alternatively, may be measured by immunological methods, such as immunohistochemical staining of cells or tissue sections and assay of cell culture or body fluids, to quantitate directly the expression of gene product. Antibodies useful for immunohistochemical staining and assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to *Anaplasma phagocytophilum* DNA and encoding a specific antibody epitope.

After expression, recombinant antigen may be recovered from culture medium or from host cell lysates. If membrane-bound, it can be released from the membrane using a suitable detergent solution (e.g. Triton-X 100) or by enzymatic cleavage. Cells employed in expression of *Anaplasm phagocytophilum* antigen can be disrupted by various physical or chemical means, such as freeze-thaw cycling, sonication, mechanical disruption, or cell lysing agents.

It may be desired to purify recombinant antigen from host cell proteins. The following procedures are exemplary of suitable purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns to bind epitope-tagged forms of the protein of interest. Various methods of protein purification may be employed and such methods are known in the art and described for example in Deutscher, *Methods in Enzymology,* 182 (1990); Scopes, Protein Purification: Principles and Practice, Springer-Verlag, New York (1982). The purification step(s) selected will depend, for example, on the nature of the production process used and the particular antigen produced.

ELISA Assay

Detection of antibody binding in IFA sero-positive sera may be accomplished by techniques known in the art, e.g., ELISA (enzyme-linked immunosorbent assay), western blots, and the like. In one embodiment, antibody binding is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

As appreciated by one skilled in the art, an enzyme-linked immunosorbent assay (ELISA) may be employed to detect antibody binding in IFA sero-positive sera. In an initial step of an ELISA, an antigen is immobilized onto a surface (for example by passive adsorption known as coating). For purposes of this application, exemplary antigens include *Anaplasma phagocytophilum* type IV secretion system proteins (eg. virB10 and virB11), hemolysin, succinate dehydrogenase and p44-8 outer membrane protein and the like. Recombinant full-length protein as well as fragments thereof may be used. Immobilization of antigen may be performed on any inert support that is useful in immunological assays. Examples of commonly used supports include small sheets, Sephadex and assay plates manufactured from polyethylene, polypropylene or polystyrene. In a preferred embodiment the immobilized antigens are coated on a microtiter plate that allows analysis of several samples at one time. More preferably, the microtiter plate is a microtest 96-well ELISA plate, such as those sold under the name Nunc Maxisorb or Immulon.

Antigen immobilization is often conducted in the presence of a buffer at an optimum time and temperature optimized by one skilled in the art. Suitable buffers should enhance immobilization without affecting the antigen binding properties. Sodium carbonate buffer (e.g., 50 mM, pH 9.6) is a representative suitable buffer, but others such as Tris-HCl buffer (20 mM, pH 8.5), phosphate-buffered saline (PBS) (10 mM, pH 7.2-7.4) are also used. Optimal coating buffer pH will be dependent on the antigen(s) being immobilized. Optimal results may be obtained when a buffer with pH value 1-2 units higher than the isoelectric point (pI) value of the protein is used. Incubation time ranges from 2-8 hours to overnight. Incubation may be performed at temperatures ranging from 4-37° C. Preferably, immobilization takes place overnight at 4° C. The plates may be stacked and coated long in advance of the assay itself, and then the assay can be carried out simultaneously on several samples in a manual, semi-automatic, or automatic fashion, such as by using robotics.

Blocking agents are used to eliminate non-specific binding sites in order to prevent unwanted binding of non-specific antibody to the plate. Examples of appropriate blocking agents include detergents (for example, Tween-20, Tween-80, Triton-X 100, sodium dodecyl sulfate), gelatin, bovine serum albumin (BSA), egg albumin, casein, non-fat dried milk and the like. Preferably, the blocking agent is BSA. Concentrations of blocking agent may easily be optimized (e.g. BSA at 1-5%). The blocking treatment typically takes place under conditions of ambient temperatures for about 1-4 hours, preferably 1.5 to 3 hours.

After coating and blocking, sera from the control (IFA sero-negative) or IFA sero-positive patients are added to the immobilized antigens in the plate. Biological sample (i.e., sera) may be diluted in buffer. Phosphate Buffered Saline (PBS) containing 0.5% BSA, 0.05% TWEEN 20 detergent may be used. TWEEN 20 acts as a detergent to reduce non-specific binding.

The conditions for incubation of the biological sample and immobilized antigen are selected to maximize sensitivity of the assay and to minimize dissociation. Preferably, the incubation is accomplished at a constant temperature, ranging from about 0° C. to about 40° C., preferably from about 22 to 25° C. to obtain a less variable, lower coefficient of variant (CV) than at, for example, room temperature. The time for incubation depends primarily on the temperature, being generally no greater than about 10 hours to avoid an insensitive assay. Preferably, the incubation time is from about 0.5 to 3 hours, and more preferably 1.5-3 hours at room temperature to maximize binding to immobilized capture antigen.

Following incubation of the biological sample and immobilized antigen, unbound biological sample is separated from the immobilized antigen by washing. The solution used for washing is generally a buffer ("washing buffer") with a pH determined using the considerations and buffers described above for the incubation step, with a preferable pH range of about 6-9. Preferably, pH is 7. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

Next, the immobilized capture antigen and biological sample are contacted with a detectable antibody at a time and temperature optimized by one skilled in the art. Detectable antibody may include a monoclonal antibody or a polyclonal antibody. These antibodies may be directly or indirectly conjugated to a label. Suitable labels include moieties that may be detected directly, such as fluorochrome, radioactive labels, and enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, horseradish peroxidase (HRP), alkaline phosphatase, and the like. Preferably, the detection antibody is a goat anti-human IgG polyclonal antibody that binds to human IgG and is directly conjugated to HRP. Incubation time ranges from 30 minutes to overnight, preferably about 60 minutes. Incubation temperature ranges from about 20-40° C., preferably about 22-25° C., with the temperature and time for contacting the two being dependent on the detection means employed.

The conjugation of such labels to the antibody, including the enzymes, is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Because IgG may occasionally interfere in IgM detection assays, IgG in patient sera may be removed prior to IgM ELISA. Ideally, an anti-human IgG antibody is used to neutralize the IgG in human sera. Commercial reagents such as GullSORB™ (Meridian Bioscience, Inc., Cincinnati, Ohio) may be used. The method for IgG removal can be conveniently optimized by one of ordinary skill in the art. For example, human sera can be incubated with anti-human IgG antibody prior to the IgM ELISA assay.

Diagnostic Kits Employing Recombinant Hemolysin Polypeptide

The present invention provides a kit for the diagnosis of *anaplasma* infection. In one embodiment, the kit is an ELISA kit containing recombinant polypeptides described herein, detection reagents including primary or secondary antibodies, and other necessary reagents including enzyme substrates and color reagents. Additional components that may be present within such kits include an instruction detailing the detection procedure for *Anaplasma phagocytophilum*, using the recombinant polypeptides of the present invention. The diagnostic kit of the present invention further comprises a positive and negative serum control. The diagnostic kit of the present invention can also be used in diagnosing other infectious diseases involving *Anaplasma phagocytophilum* such as Human Granulocytic Anaplasmosis (HGA).

The following Examples are offered by way of illustration and not by way of limitation.

EXPERIMENTAL STUDIES

The present inventors discovered that hemolysin and its protein fragments thereof serve as good candidate biomarkers for the diagnosis of *Anaplasma phagocytophilum* infection. Evidence is presented herein to demonstrate that recombinantly expressed hemolysin or hemolysin protein fragments, when immobilized in an ELISA assay, is a good detection marker for an IgG/IgM antibody response to *Anaplasma phagocytophilum* infection.

Example 1

Cloning and Expression of Hemolysin

PCR Amplification and Ligation into Plasmid Vector

In order to determine if hemolysin possesses antibody recognition sites, we cloned and recombinantly expressed the full-length hemolysin protein in *Anaplasma phagocytophilum*.

Our cloning strategy involved the design and preparation of synthetic oligonucleotides (~30 bp in length) and use of them in amplifying the hemolysin gene. As controls, we also cloned two (2) non-TIVSS proteins (i.e., succinate dehydrogenase iron-sulfur subunit and p44 outer membrane protein) and used them for comparison. Table 1 shows the nucleotide sequence of the various oligonucleotides (i.e., SEQ ID NOs: 1-6) used in the PCR amplification reaction.

Genomic DNA of *Anaplasma phagocytophilum* (a generous gift from Dr. S. Dumler at Johns Hopkins University) was used as the template for each of the PCR reactions. Synthetic oligonucleotides corresponding to the hemolysin gene were used for the PCR amplification reactions. Using the synthetic oligonucleotides (sequence listed in Table 1) and genomic DNA from *Anaplasma phagocytophilum*, we successfully amplified the hemolysin gene; as well as two (2) non-hemolysin genes (i.e., succinate dehydrogenase iron-sulfur and p44 proteins) (See, FIGS. 2 and 3).

Figure 2:
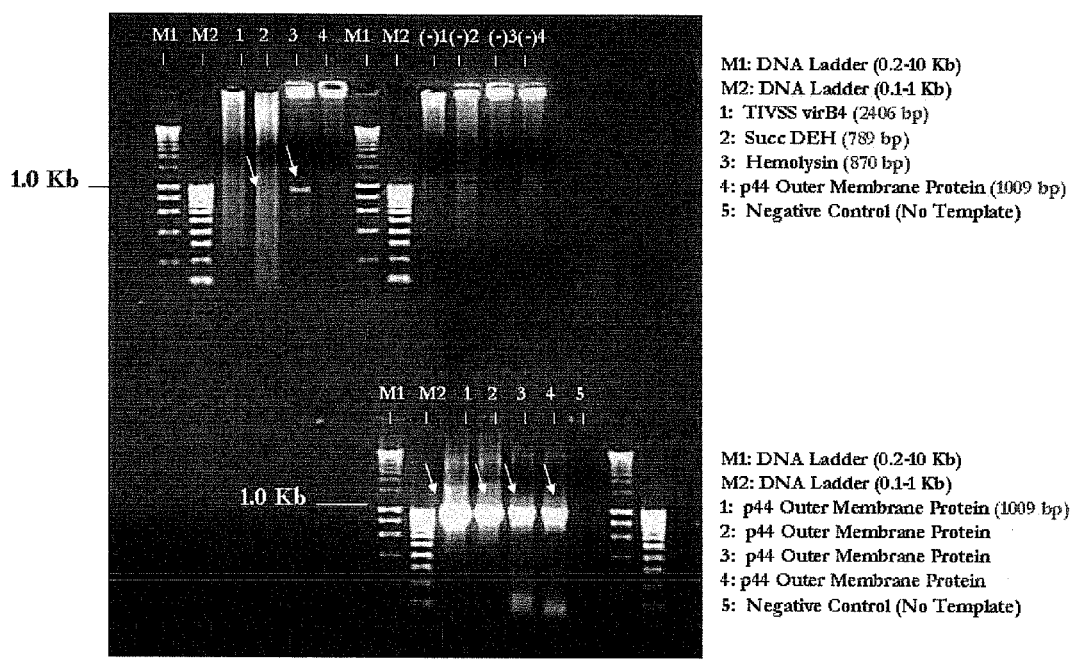
FIG. 2 depicts the EK/LIC PCR Amplification of *Anaplasma* Genes Encoding Hemolysin (lane 3, upper panel), p44 (lanes 1-4, lower panel), and Succinate Dehydrogenase Iron Sulfur (lane 2, upper panel) Proteins of *Anaplasma phagocytophilum*.

FIG. 2 shows an agarose gel of the amplified genes prior to processing of the PCR reactions in preparation for ligation into pET30 vector. The hemolysin amplicon having an expected size is shown by the arrow in this figure. In preparation for ligation with the vector, the PCR amplification reactions were treated to remove any remaining nucleotides, primers, and reaction components.

Figure 3:
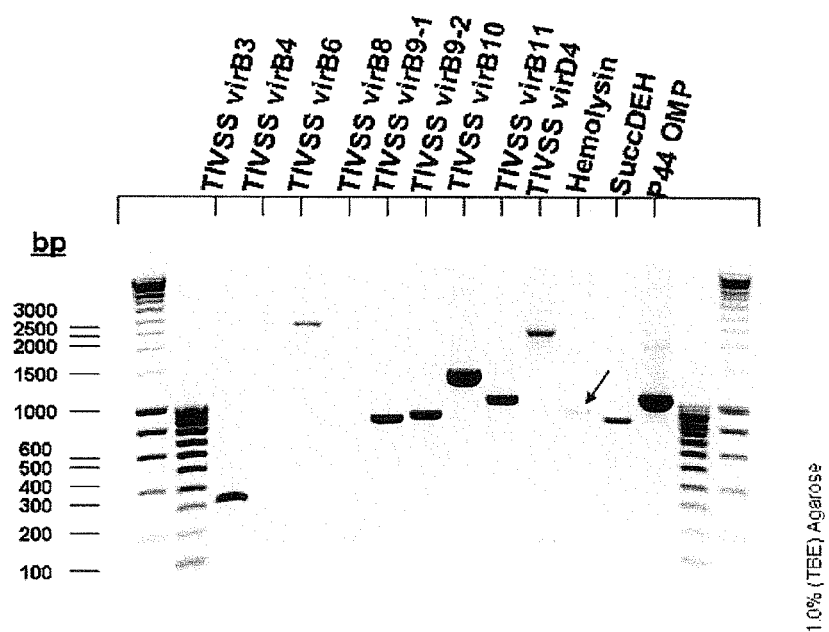
FIG. 3 depicts the Post-PCR Clean-Up of *Anaplasma* Clones for Recombinant Expression. The AITOW in this Figure Shows the Hemolysin Amplicon.

FIG. 3 shows a Coomassie-stained gel of the amplified genes following clean-up of the PCR reactions. The arrow in this figure shows the hemolysin amplicon of expected size. The resulting PCR products were then treated with T4 DNA polymerase and ligated into pET30 using standard protocols. Ligation of the hemolysin insert DNA (including succinate dehydrogenase iron-sulfur and p44 protein insert DNAs) was performed as described below.

T4 Polymerase Treatment of PCR Products and Ligation into pET30 Vector

In order to ligate the cloned insert DNA with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicon into the expression vector to form pET30/insert DNA.

Figure 4:
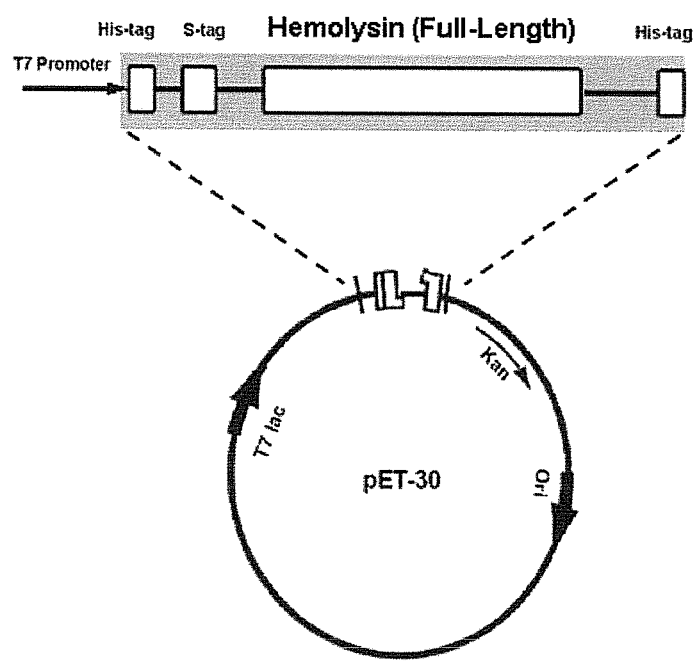
FIG. 4 depicts the pET30 Vector Containing the Full-Length Hemolysin Gene.

FIG. 4 depicts the pET30 vector containing the inserted gene (e.g., full-length hemolysin, succinate dehydrogenase iron-sulfur and p44). The nucleotide sequences of hemolysin, succinate dehydrogenase iron-sulfur and p44 are publicly available and their accession numbers are listed in Table 1.

Transformation of Recombinant Clones into NovaBlue *E. coli*

In these series of experiments, we transformed the ligated DNAs (annealing reaction) into host bacterial cells (NovaBlue *E. coli*). The ligated DNA was hemolysin amplicons as well as succinate dehydrogenase iron-sulfur and p44 amplicons. We chose NovaBlue *E. coli* because this bacterial strain is optimized for producing a stable cell line containing a recombinant insert (see, Novagen Ek/LIC manual). Transformation into NovaBlue competent *E. coli* (Novagen) was performed using standard protocols. First, appropriate numbers of 20 µl aliquots of competent cells were prepared from −80° C., and allowed to thaw on ice for several minutes, followed by the addition of 1 µl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM MgCl$_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

Colony PCR of NovaBlue Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

Figure 6:
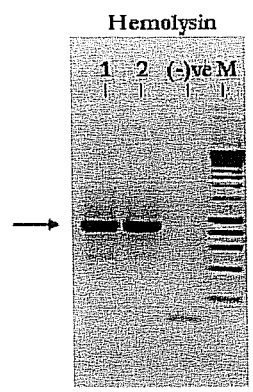
FIG. 6 depicts the Colony PCR of Hemolysin Transformants in NovaBlue E. coli.

FIG. 6 shows agarose gel electrophoresis analysis of two hemolysin transformants in NovaBlue *E. coli*. Amplicons of expected size (~800 bp) (arrow) were observed following analysis of the PCR reactions. NovaBlue *E. coli* colonies containing the pET30/insert DNA were further cultured in LB-kanamycin broth (for the isolation of plasmids).

Plasmid Mini-Preps

In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed *E. coli*. Wizard Plus SV Minipreps DNA Purification system (Promega) was used according to the manufacturer's recommended protocol. The concentration (1 OD$_{260/280}$=0.5 mg/ml) and the relative purity (OD$_{260/280}$) of the isolated plasmid DNA preparations were determined by spectrophotometric analysis.

Sequencing Analysis of Insert DNA

We next performed sequence analysis on the isolated plasmid DNA using the Applied BioSystems 3130 Genetic Analyzer DNA Sequencing instrument. All of the insert DNAs were confirmed to be accurate by BLAST analysis and in-frame. For example, the sequence analysis of the isolated plasmid DNA for hemolysin is summarized in FIG. 5. FIG. 5 depicts polynucleotide sequence encoding hemolysin, together with its deduced amino acid sequence. BLAST (Basic Local Alignment Search Tool) analysis of the sequence confirmed a match between the nucleotide and deduced amino acid sequences and the published sequence of *Anaplasma phagocytophilium* (Putative) hemolysin.

Transformation of BL21 (DE3) *E. coli* with Recombinant Plasmids

After confirmation of the obtained recombinant plasmids, we proceeded to transform them into BL21 (DE3) competent *E. coli* (Novagen). Transformation was carried out by removing the appropriate number of 20 µl aliquots of competent cells from −80° C., allowing the tubes to thaw on ice for several minutes, followed by the addition of 1 µl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

Colony PCR of BL21 (DE3) Transformants

Figure 7:
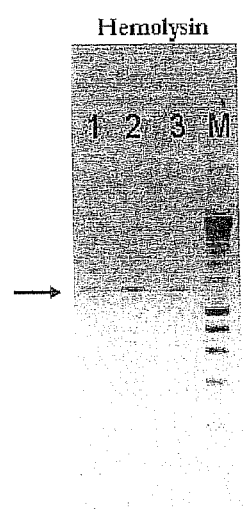
FIG. 7 depicts the Colony PCR of Hemolysin Transformants in BL21 (DE3) E. coli.

To confirm the successful transformation of recombinant pET30/insert DNA in BL21 (DE3) *E. coli* cells, we selected several colonies of each transformant grown on LB plates (with kanamycin), and performed colony PCR using forward and reverse vector-specific primers. An aliquot of each PCR reaction was analyzed using agarose gel electrophoresis. FIG. 7 shows agarose gel electrophoresis analysis of three (3) of hemolysin transformants in BL21 (DE3) *E. coli*. Amplicons of expected size (~1,100 bp) (arrow) were observed following analysis of the PCR reactions. Several BL21 (DE3) *E. coli* colonies containing the pET30/insert DNA were then processed for recombinant expression.

In addition to hemolysin, we also confirmed the successful transformation of recombinant pET30/insert DNA for control inserts (i.e., succinate dehydrogenase iron-sulfur and p44).

Expression of Recombinant Hemolysin Protein in *E. coli*

Figure 8:
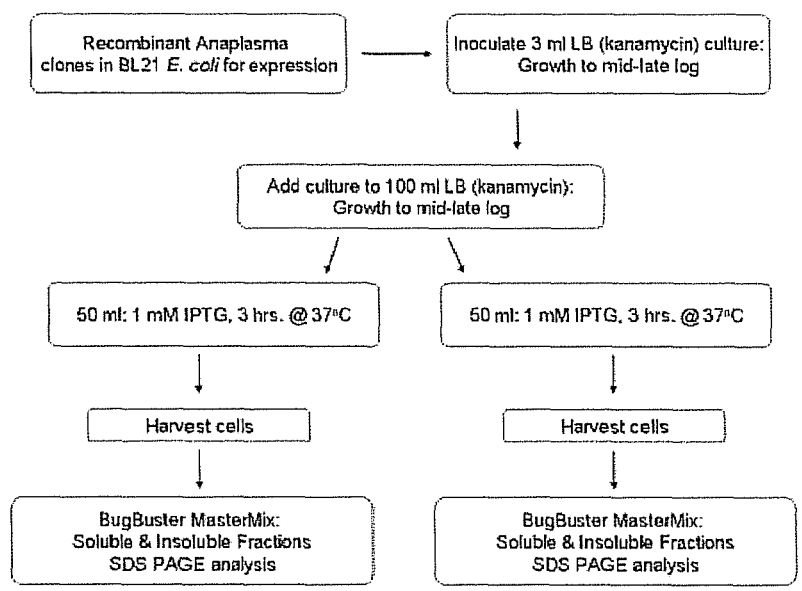
FIG. 8 depicts the Protocol for IPTG-Induced Recombinant Hemolysin Protein Expression in BL21 E. coli.
Figure 9:
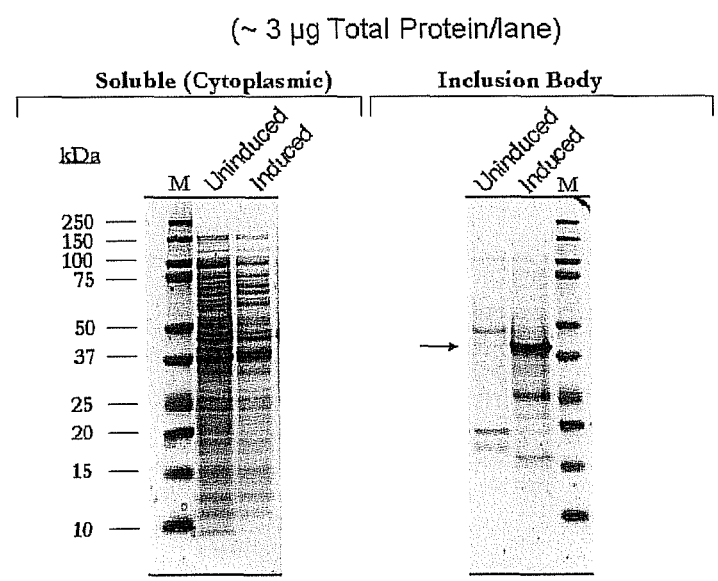
FIG. 9 depicts the IPTG Induction of Hemolysin Protein (Soluble vs. Insoluble Fractions).

FIG. 8 depicts a flow chart depicting the steps for IPTG induction of recombinant hemolysin protein in BL21 *E. coli*. For expression of recombinant hemolysin (rHemolysin) protein, BL21 (DE3) *E. coli* were transformed with the pET30-rHemolysin plasmid DNA containing the hemolysin amplicon. The pellet was then processed to isolate the insoluble cytoplasmic fraction, which consists of cell debris and aggregated protein (inclusion bodies). Inclusion body purification was carried out by re-suspending the pellet in the same volume (5 ml) of 1× BugBuster Master Mix used to re-suspend the original cell pellet. The mixtures were vortexed, followed by the addition of 20 ml of 1:10 diluted BugBuster Master Mix. The suspensions were vortexed, and then centrifuged at 5,000×g for 15 minutes at 4° C. to collect the inclusion body fraction. The pellets were re-suspended in 15 ml of 1:10 diluted BugBuster Master Mix, vortexed, and centrifuged at 5,000×g for 15 min. at 4° C. This step was repeated, with the centrifugation carried out for 15 minutes at 16,000×g. The supernatant was discarded, and the pellets re-suspended in 500 µl of PBS. An aliquot of the soluble and insoluble (inclusion body) fractions were analyzed on an SDS PAGE gel (FIG. 9).

Figure 10:
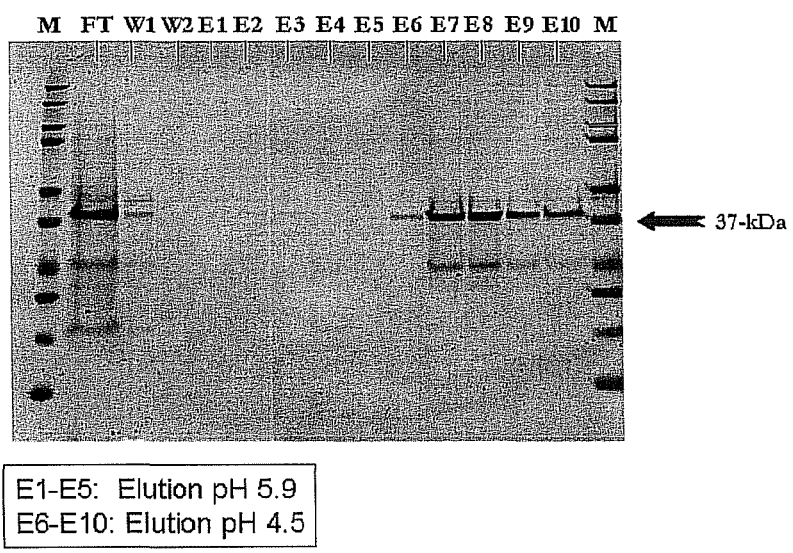
FIG. 10 depicts the Ni-NTA Purification of 6×His-Tagged Recombinant Hemolysin.

Purification of Recombinant Recombinant Hemolysin Protein Under Urea Denaturing Conditions The recombinant protein present within the inclusion body pellets was resuspended in 4 ml of denaturing lysis/binding buffer. To this mixture was added 1 ml of Ni-NTA His•Bind slurry (Novagen). The suspension was mixed gently on a rotating shaker for 1 hr. The lysate-resin mixture was carefully loaded onto a column placed over a 15 ml conical tube, and the flow-through collected and saved for later analysis. The column was washed with 4 ml of wash buffer collected in another 15 ml conical tube, and the fraction saved for later analysis (labeled as W1 in FIG. 10). The column was washed again with 4 ml of wash buffer, and the fraction saved for later analysis (labeled as W2 in FIG. 10). The recombinant protein was eluted with 5×0.5 ml of elution buffer (pH 5.9), and each fraction set aside for later analysis (labeled as E1-E5 in FIG. 10). Additional elutions were carried out with 5×0.5 ml of elution buffer (pH 4.5), and each fraction set aside for later analysis (labeled as E6-E10 in FIG. 10).

Buffer Compositions (all buffers were prepared fresh immediately prior to being used):

Lysis Buffer with Urea 100 mM Phosphate buffer 10 mM Tris-Cl

8 M urea

Buffer pH adjusted to 8.0

Wash Buffer with Urea 100 mM Phosphate buffer 10 mM Tris-Cl

8 M urea

Buffer pH adjusted to 6.3

Elution Buffer with Urea (pH 5.9)

100 mM Phosphate buffer 10 mM Tris-Cl

8 M urea

Buffer pH adjusted to 5.9
Elution buffer with urea (pH 4.5)
100 mM Phosphate buffer
10 mM Tris-Cl
8 M urea
Buffer pH adjusted to 4.5

Example 2

IgG/IgM ELISA for Recombinantly Expressed Hemolysin Protein

We adopted IgG and IgM ELISA assays and evaluated the binding activity of the recombinant protein towards IgG and IgM. The ELISA procedure involves: (i) coating 96-well micro-titer plates with the recombinant protein at varying concentrations at 4° C. overnight; (ii) adding 5% non-fat milk to block non-specific binding; (iii) adding patients' sera to allow formation of antibody-antigen complex; (iv) detecting the antibody-antigen complex. IFA sero-positive sera served as positive controls, and IFA sero-negative sera served as negative controls. Detection of antibody-antigen complex was performed with the use of horseradish peroxidase.

Patient Study:
Hemolysin
IgG ELISA

Figure 11:
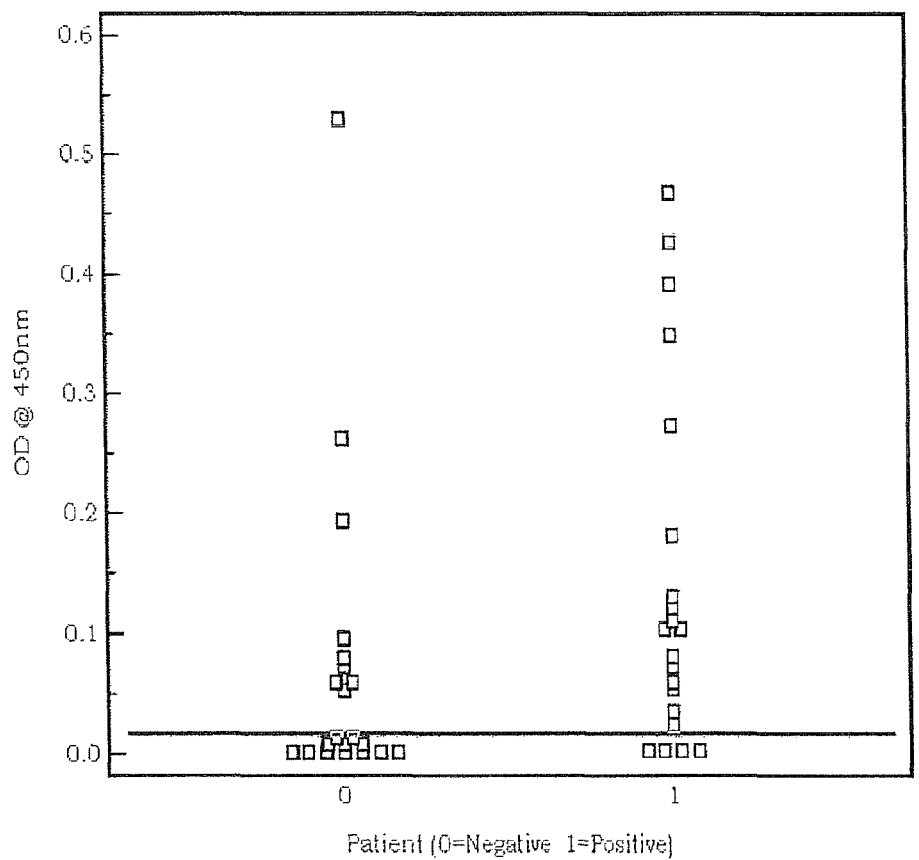
FIG. 11 depicts the IgG ELISA for Recombinant Hemolysin of *Anaplasma phagocytophilum*.

Recombinant hemolysin protein, when tested in an IgG ELISA, exhibited a dose-dependent increase in binding towards IgG sero-positive serum as measured by $OD_{450}$ nm. IgG ELISA for recombinant hemolysin attained a sensitivity of 81.0% and a specificity of 57.1% (FIG. 11).

ROC Analysis

Figure 12:
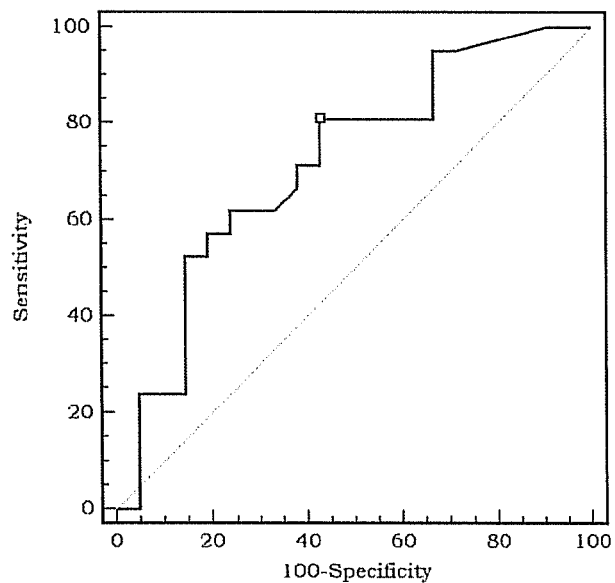
FIG. 12 depicts the ROC Analysis for Recombinant Hemolysin IgM ELISA.

The raw IgG ELISA data for hemolysin was analyzed with ROC curve determination using MedCalc statistical software. Performance analysis of ROC curve is shown in FIG. 12. AUC of recombinant hemolysin is 0.718 (95% confidence interval; range: 0.558 to 0.845).

IgM ELISA

Figure 13:
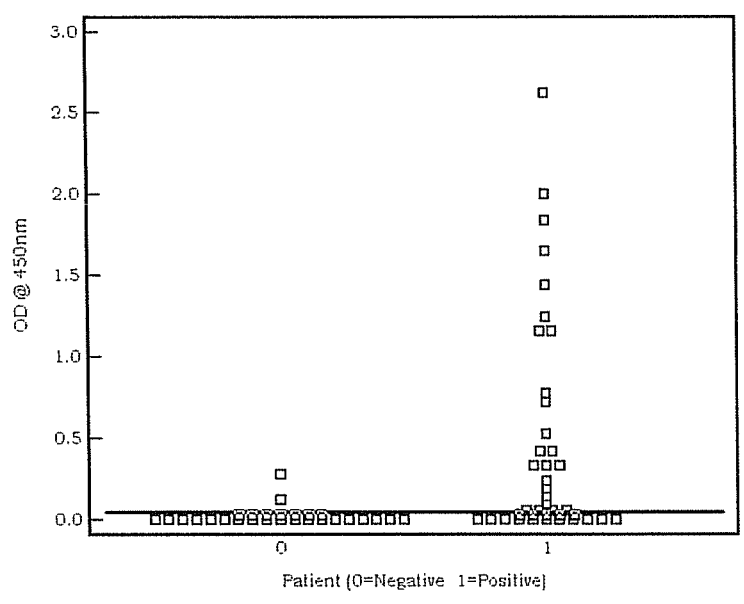
FIG. 13 depicts the IgM ELISA for Recombinant Hemolysin of *Anaplasma phagocytophilum*.

In this series of studies, we examined recombinant hemolysin in IgM ELISA. Recombinant hemolysin protein exhibited a dose-dependent increase in binding towards IgM sero-positive serum (as measured by $OD_{450}$ nm) IgM ELISA for recombinant hemolysin attained a sensitivity of 60.0% and a specificity of 92.9% (FIG. 13).

ROC Analysis

Figure 14:
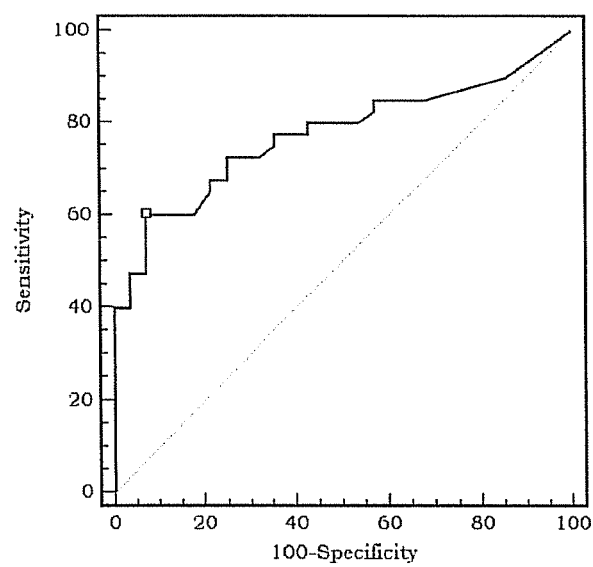
FIG. 14 depicts the ROC Analysis for Recombinant Hemolysin IgM ELISA.
Figure 15:
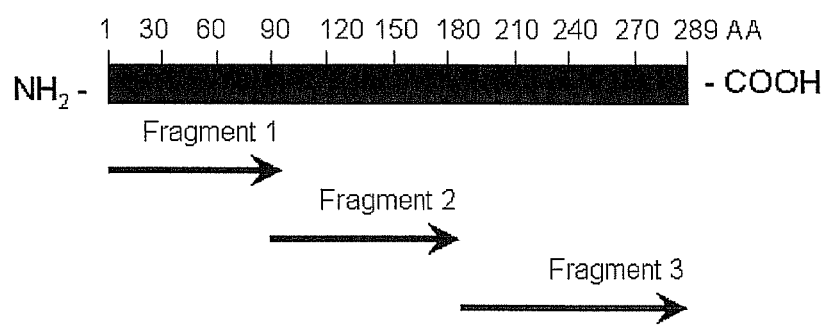
FIG. 15 depicts the Relationship of Recombinant Hemolysin Fragments 1-3 to the Full-Length Hemolysin Protein.

The raw IgM ELISA data for hemolysin was analyzed with ROC curve determination using MedCalc statistical software. Performance analysis of ROC curve is shown in FIG. 14. AUC of recombinant hemolysin is 0.773 (95% confidence interval; range: 0.656 to 0.866).

Table 3 summarizes IgG and IgM ELISA data for hemolysin.

Example 3

Amplification and Cloning of Hemolysin Protein Fragments

I) PCR Amplification and Ligation into Plasmid Vector

We cloned and recombinantly expressed hemolysin fragments 1-3 in *E. coli*. Our cloning strategy involved the design and preparation of synthetic oligonucleotides (~30 bp in length) and use of them in amplifying the hemolysin fragments.

Table 4 shows the nucleotide sequence of the various oligonucleotides (i.e., SEQ ID NOs. 10-15) used in the PCR amplification reaction.

Genomic DNA of *Anaplasma phagocytophilum* (a generous gift from Dr. S. Dumler at Johns Hopkins University) was used as the template for each of the PCR reactions. Synthetic oligonucleotides corresponding to the hemolysin gene fragments were used for the PCR amplification reactions. Using the synthetic oligonucleotides (sequence listed in Table 4) and genomic DNA from *Anaplasma phagocytophilum*, we successfully amplified the hemolysin gene fragments; as well as two (2) non-TIVSS genes (i.e., succinate dehydrogenase iron-sulfur and p44 proteins) (See, FIGS. 5 and 6).

Agarose gel analysis performed on the amplified genes confirmed that the PCR products obtained for each of the fragments were of the correct size. In preparation for ligation with the vector, the PCR amplification reactions were treated to remove any remaining nucleotides, primers, and reaction components. The resulting PCR products were then treated with T4 DNA polymerase and ligated into pET30 using standard protocols.

II) T4 Polymerase Treatment of PCR Products and Ligation into pET30 Vector

Figure 16:
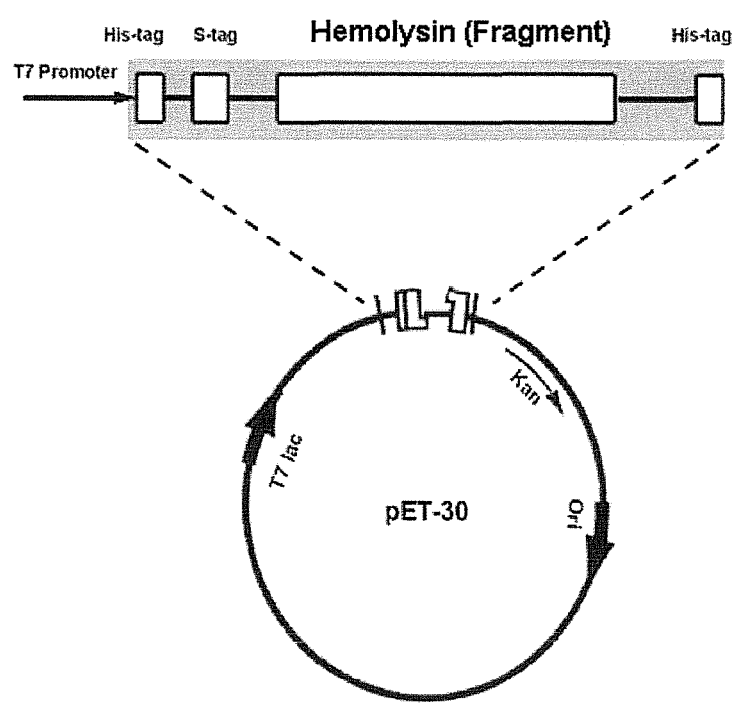
FIG. 16 depicts the pET30 Vector Containing the Hemolysin Gene Fragment.
Figure 20:
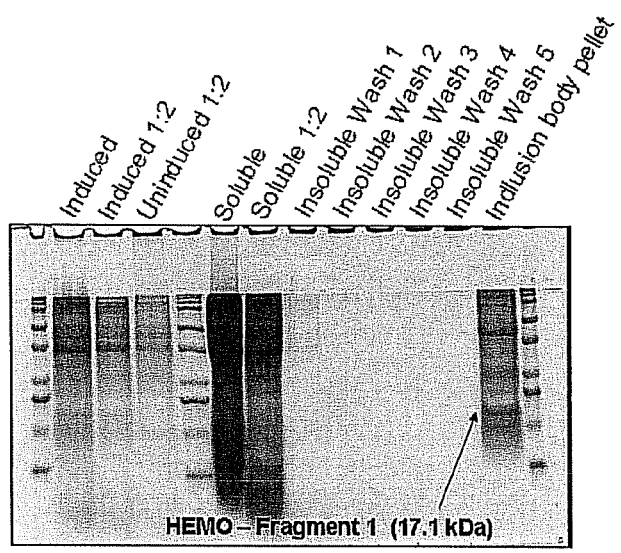
FIG. 20 depicts the Induction of Hemolysin Fragment 1, and the Presence of the Recombinant Protein Within the Insoluble (Inclusion Body) Fraction (Arrow).
Figure 21:
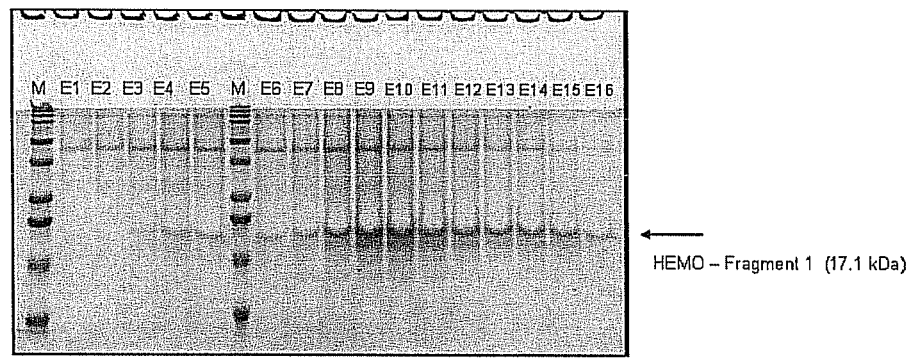
FIG. 21 depicts the Nickel Column Purification of Hemolysin Fragment 1.

In order to ligate the cloned insert DNAs with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicons into the expression vector to form pET30/insert DNA. FIG. 16 depicts the pET30 vector containing the inserted genes (Fragments 1-3).

III) Transformation of Recombinant Clones into NovaBlue *E. coli*

In these series of experiments, we transformed the ligated DNAs (annealing reaction) into host bacterial cells (NovaBlue *E. coli*). The ligated DNAs were hemolysin fragments 1-3 amplicons. We chose NovaBlue *E. coli* because this bacterial strain is optimized for producing a stable cell line containing a recombinant insert (see, NovaBlue Ek/LIC manual). Transformation into NovaBlue competent *E. coli* (Novagen) was performed using standard protocols. First, appropriate numbers of 20 µl aliquots of competent cells were prepared from −80° C., and allowed to thaw on ice for several minutes, followed by the addition of 1 µl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM $MgCl_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

IV) Colony PCR of NovaBlue Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

Agarose gel electrophoresis analysis was performed for eight hemolysin transformants in NovaBlue *E. coli*. Amplicons of expected size were observed following analysis of the PCR reactions. NovaBlue *E. coli* colonies containing the pET30/insert DNA were further cultured in LB-kanamycin broth (for the isolation of plasmids).

V) Plasmid Mini-Preps

In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed E. coli. Wizard Plus SV Minipreps DNA Purification system (Promega) was used according to the manufacturer's recommended protocol. The concentration (1 $OD_{260/280}$=0.5 mg/ml) and the relative purity ($OD_{260/280}$) of the isolated plasmid DNA preparations were determined by spectrophotometric analysis.

VI) Sequencing Analysis of Insert DNA

We next performed sequence analysis on the isolated plasmid DNA using the Applied BioSystems 3130 Genetic Analyzer DNA Sequencing instrument. All of the insert DNA were confirmed to be accurate by BLAST analysis and in-frame. As examples, the sequence analysis of the isolated plasmid DNA and the deduced amino acid sequences for hemolysin fragment 1, fragment 2, and fragment 3 are summarized in FIGS. 17-19, respectively. BLAST (Basic Local Alignment Search Tool) analysis of the sequences confirmed a match between each of the nucleotide sequences and the published sequences of the *Anaplasma phagocytophilium* hemolysin genes.

VII) Transformation of BL21 (DE3) E. coli with Recombinant Plasmids

After confirmation of the obtained recombinant plasmids, we proceeded to transform them into BL21 (DE3) competent E. coli (Novagen). Transformation was carried out by removing the appropriate number of 20 µl aliquots of competent cells from −80° C., allowing the tubes to thaw on ice for several minutes, followed by the addition of 1 µl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

VIII) Colony PCR of BL21 (DE3) Transformants

To confirm the successful transformation of recombinant pET30/insert DNA in BL21 (DE3) E. coli cells, we selected several colonies of each transformant grown on LB plates (with kanamycin), and performed colony PCR using forward and reverse vector-specific primers. An aliquot of each PCR reaction was analyzed using agarose gel electrophoresis. FIG. 7 shows agarose gel electrophoresis analysis of three (3) of hemolysin transformants in BL21 (DE3) E. coli. Amplicons of expected size (1,100 bp) (arrow) were observed following analysis of the PCR reactions. Several BL21 (DE3) E. coli colonies containing the pET30/insert DNA were then processed for recombinant expression.

In addition to hemolysin, we also confirmed the successful transformation of recombinant pET30/insert DNA for control inserts (i.e., succinate dehydrogenase iron-sulfur and p44).

Example 4

Expression and Purification of Hemolysin Protein Fragments

I) Expression of Recombinant Hemolysin Fragments 1-3 in *E. coli*

In order to express fragments 1-3 of hemolysin, the Overnight Express™ Autoinduction System 1 (Novagen) was used. In each 500 ml flask (one baffled and one flat bottom per fragment), 110 ml of LB broth was added. From the Autoinduction kit, 0.02 volume of OnEx™ Solution 1, 0.05 volume of OnEx Solution 2, and 0.001 volume of OnEx Solution 3 were added to 1 volume Lb medium (glucose free). Kanamyacin was added to a final concentration of 30 µg/ml. LB medium was inoculated with isolated colonies from the plates, and incubated overnight (approximately 16 hours) at 37° C. with shaking at 250 rpm.

The following day, each culture of the fragments was spun down for 10 minutes at 10,000×g. The supernatant was decanted, and 15 ml of Bugbuster Master Mix (Novagen) was used to re-suspend each pellet thoroughly. The cell suspension was incubated in room temperature on a shaker at slow speed for 20 minutes, and was then centrifuged at 4° C. at 16,000×g for 20 minutes to separate the soluble cytoplasmic fraction (supernatant) from the insoluble cytoplasmic fraction (pellet). The pellets were re-suspended in 15 ml Bugbuster, after which 6 volumes of 1:10 diluted Bugbuster was added to each and then vortexed for 1 minute. The re-suspension was centrifuged at 4° C. at 5,000×g for 15 minutes, and the supernatant was saved as an insoluble wash. The pellet was resuspended in half the original culture volume of 1:10 diluted Bugbuster, mixed by vortexing, and centrifuged at 4° C. at 5,000×g for 15 minutes. This step was repeated twice, with the final spin at 16,000×g. The pellets (inclusion bodies) were then kept at −70° C. until needed for further purification. The soluble cytoplasmic fractions and the insoluble washes were analysed on SDS-PAGE gels, which showed that fragments 1 and 2 were found in the insoluble fractions (inclusion body), and fragment 3 was present predominantly in the soluble fraction.

For purification of fragment 3 from the soluble fraction, Ni-NTA Buffer Kit (Novagen) and Ni-NTA His•Bind Resin (Novagen) were used. In order to equilibrate the resin, 30 ml 1× Binding Buffer (equal to the amount of the soluble fraction) was added to 5 ml resin, and the mixture was incubated on a shaker in 4° C. for 10 min, prior to the tubes being placed in an upright position at room temperature to facilitate the settling of the resin at the bottom of the tubes. 30 ml of the Binding Buffer from the top was taken out and replaced with the soluble fraction. The resin/soluble fraction mixture was then incubated on a shaker at 4° C. for 1 hour. The mixture was then decanted into an empty column. Using a slow drip, the flow-through was collected. Taking careful steps to avoid allowing the resin to become dry at any time, 4 ml or 1× Wash buffer was added twice. Lastly, 5×0.5 ml of 1× Elution Buffer was added to the resin to collect the protein. The flow-through, wash buffers and elution buffers were analyzed on an SDS-PAGE gel to confirm the successful purification of the proteins, and to determine in which fractions the proteins were eluted.

II) Purification of Recombinant Hemolysin Fragments 1 and 2 Under Urea Denaturing Conditions The inclusion body fractions containing recombinant fragments 1 and 2 were purified under urea denaturing conditions as previously described for full-length hemolysin and p44 proteins using freshly prepared buffers containing urea. For fragment purification, an additional buffer (pH 5.0), whose composition is shown below, was added to the purification protocol.

Elution Buffer with Urea (pH 5.0)
100 mM Phosphate buffer
10 mM Tris-Cl
8 M urea
Buffer pH adjusted to 5.0

Example 5

IgG ELISA for Recombinant Hemolysin Protein Fragments

We adopted IgG ELISA assays and evaluated the binding activity of the recombinant fragments towards IgG. The ELISA procedure involves: (i) coating 96-well micro-titer plates with the recombinant protein fragments at varying concentrations at 4° C. overnight; (ii) adding 5% non-fat milk to block non-specific binding; (iii) adding patients' sera to allow formation of antibody-antigen complex; (iv) detecting the antibody-antigen complex. IFA sero-positive sera served as positive controls, and IFA sero-negative sera served as negative controls. Detection of antibody-antigen complex was performed with the use of horseradish peroxidase.

Patient Study:
Hemolysin Fragments 1-3
Fragment 1

Figure 22:
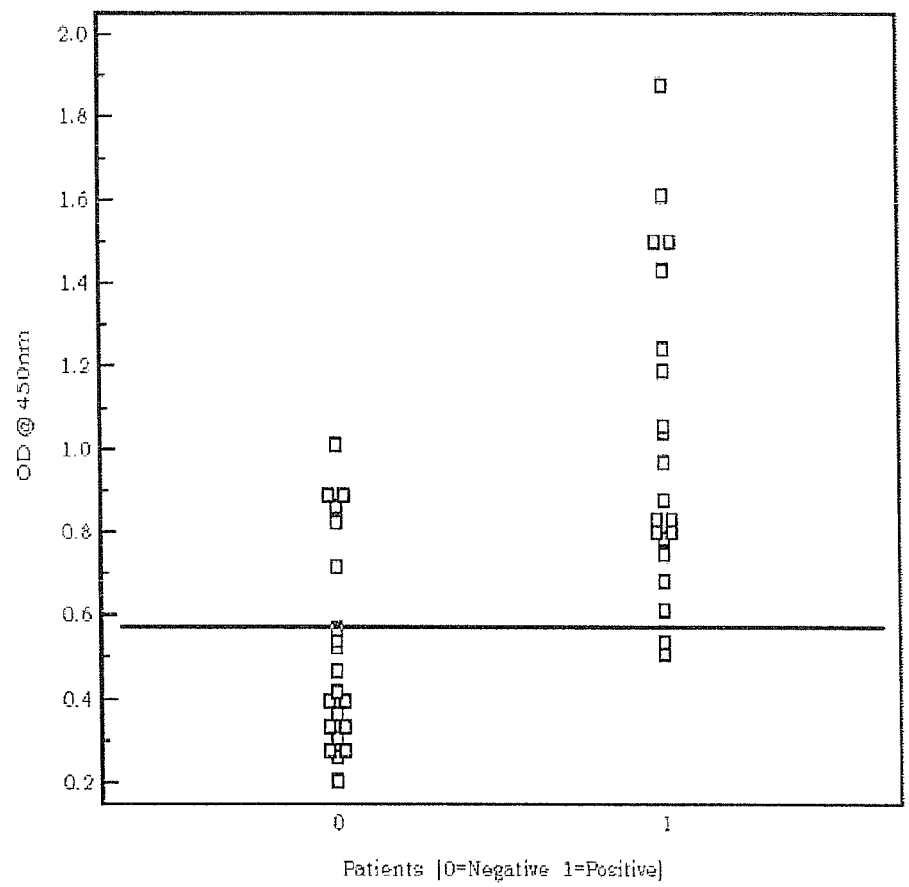
FIG. 22 depicts the IgG ELISA for Recombinant Hemolysin Fragment 1.

Fragment 1 exhibited a dose-dependent increase in binding towards IgG sero-positive serum (as measured by $OD_{450}$ nm). IgG ELISA for recombinant fragment 1 attained a sensitivity of 90.5% and a specificity of 71.4% (FIG. 22).

ROC Analysis

Figure 23:
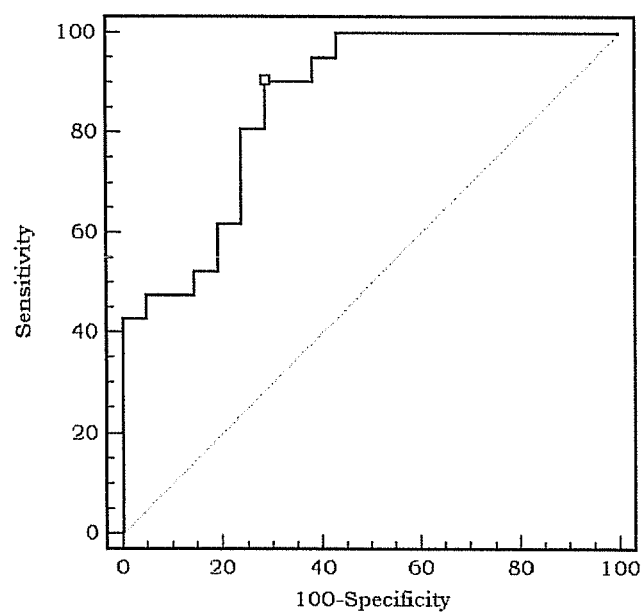
FIG. 23 depicts the ROC Analysis for Recombinant Fragment 1 IgG ELISA.
Figure 24:
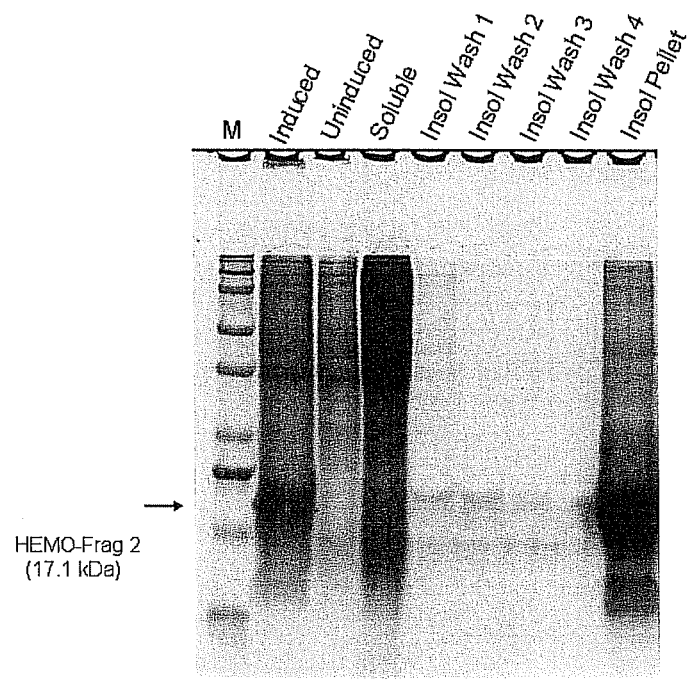
FIG. 24 depicts the Induction of Hemolysin Fragment 2, and the Presence of the Recombinant Protein Within the Insoluble (Inclusion Body) Fraction (Arrow).
Figure 25:
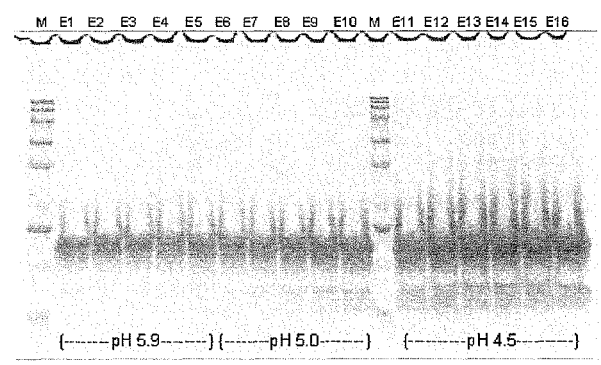
FIG. 25 depicts the Nickel Column Purification of Hemolysin Fragment 2.

The raw IgG ELISA data for fragment 1 was analyzed with ROC curve determination using MedCalc statistical software. Performance analysis of ROC curve is shown in FIG. 23. AUC of recombinant fragment 1 is 0. 0.862 (95% confidence interval; range: 0.720 to 0.948), Fragment 2

Figure 26:
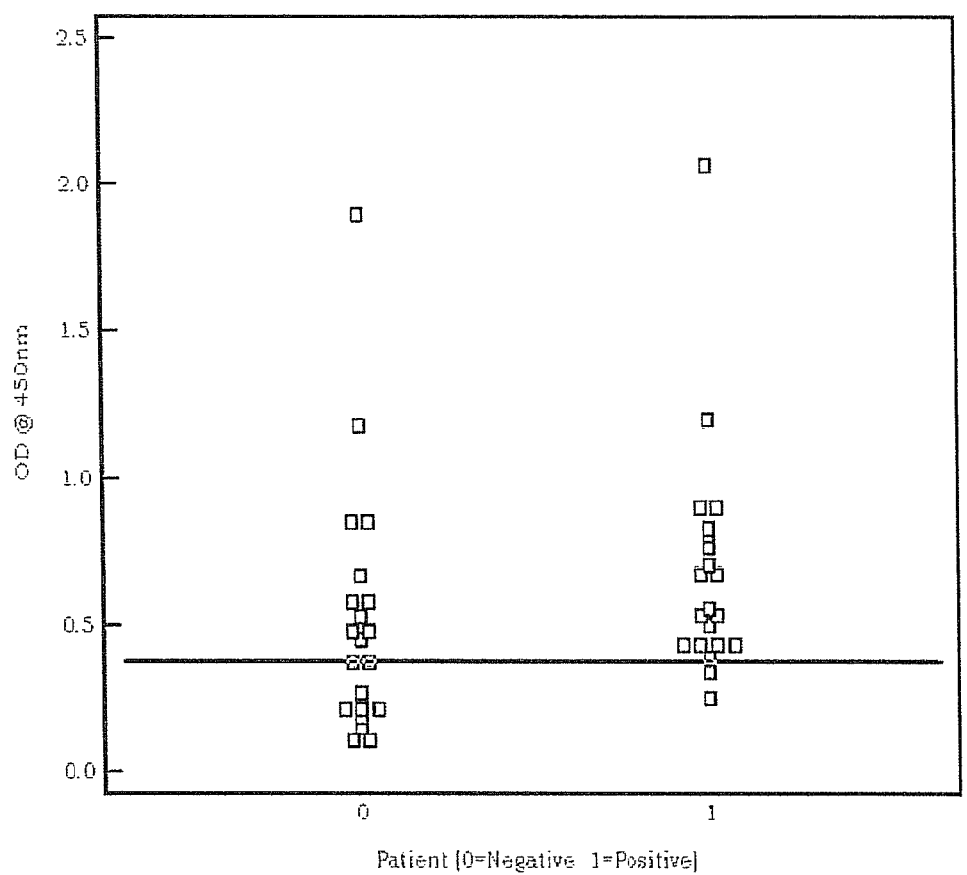
FIG. 26 depicts the IgG ELISA for Recombinant Hemolysin Fragment 2.

Fragment 2 exhibited a dose-dependent increase in binding towards IgG sero-positive serum (as measured by $OD_{450}$ nm) IgG ELISA for recombinant fragment 1 attained a sensitivity of 90.5% sensitivity and a specificity of 47.6% (FIG. 26).

ROC Analysis

Figure 27:
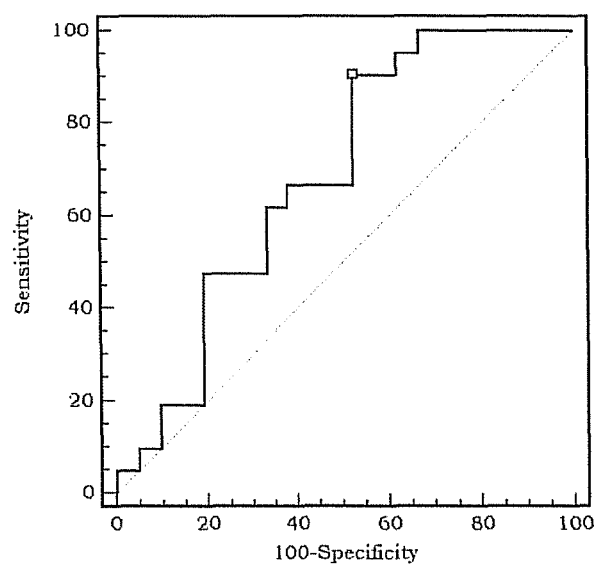
FIG. 27 depicts the ROC Analysis for Recombinant Fragment 2 IgG ELISA.
Figure 28:
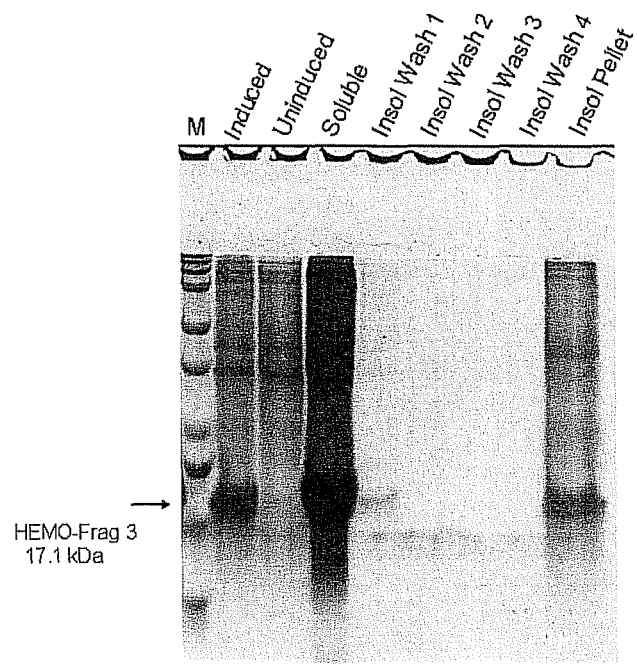
FIG. 28 depicts the Induction of Hemolysin Fragment 3, and the Presence of the Recombinant Protein Within the Insoluble (Inclusion Body) Fraction (Arrow).
Figure 29:
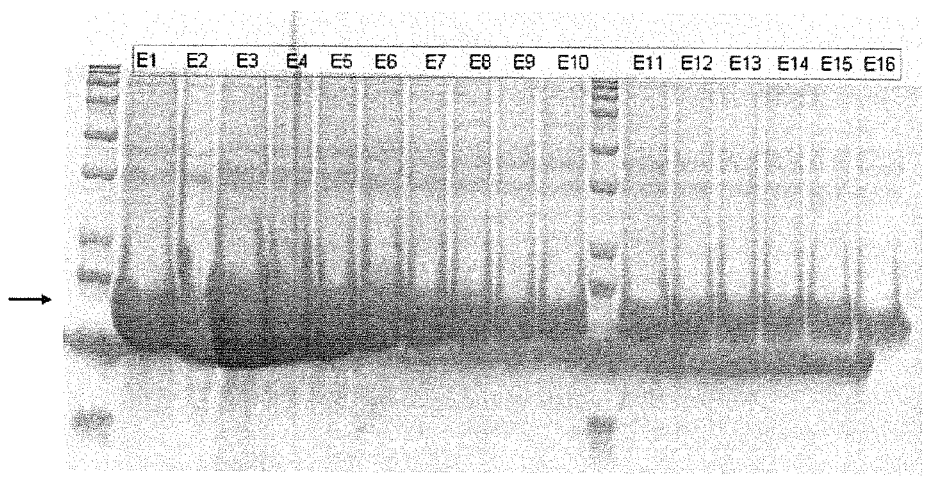
FIG. 29 depicts the Nickel Column Purification of Hemolysin Fragment 3.

The raw IgG ELISA data for fragment 2 was analyzed with ROC curve determination using MedCalc statistical software. Performance analysis of ROC curve is shown in FIG. 27. AUC of recombinant fragment 1 is 0.683 (95% confidence interval; range: 0.521 to 0.817).

Fragment 3

Figure 30:
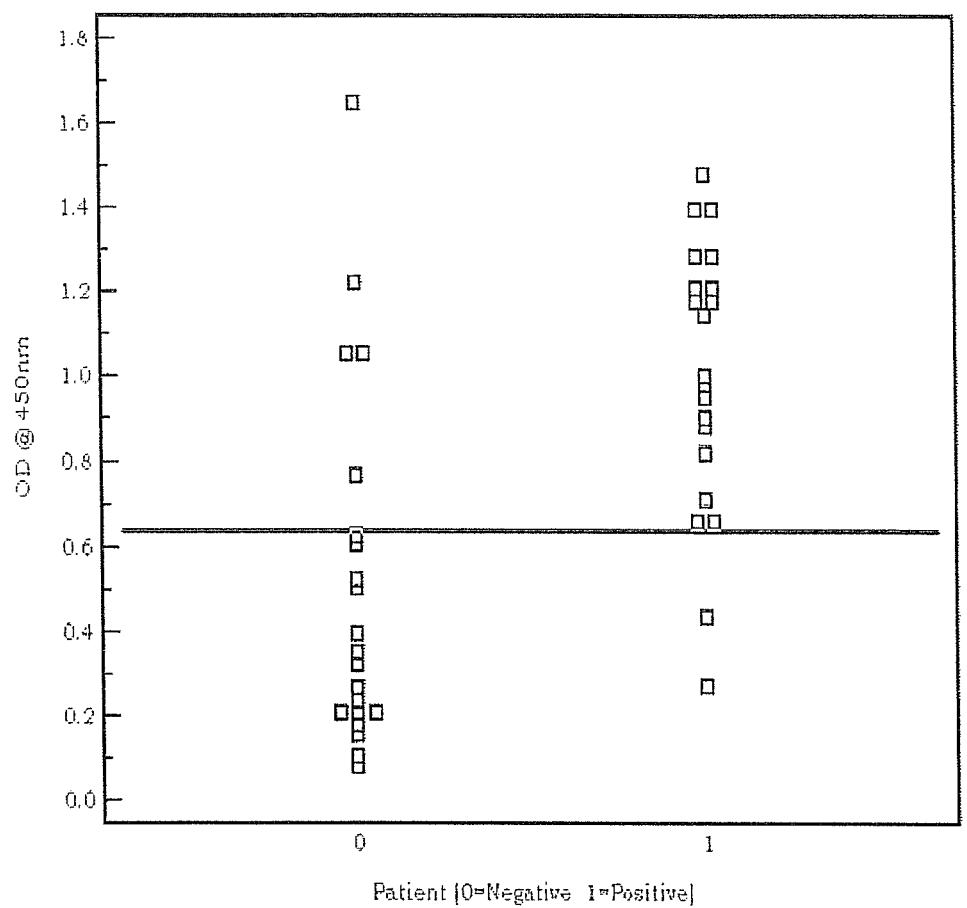
FIG. 30 depicts the IgG ELISA for Recombinant Hemolysin Fragment 3.

Recombinant fragment 3, when tested in an IgG ELISA, exhibited a dose-dependent increase in binding towards IgG sero-positive serum as measured by $OD_{450}$ nm. IgG ELISA for recombinant fragment 3 attained a sensitivity of 90.5% sensitivity and a specificity of 75.2% (FIG. 30).

ROC Analysis

Figure 31:
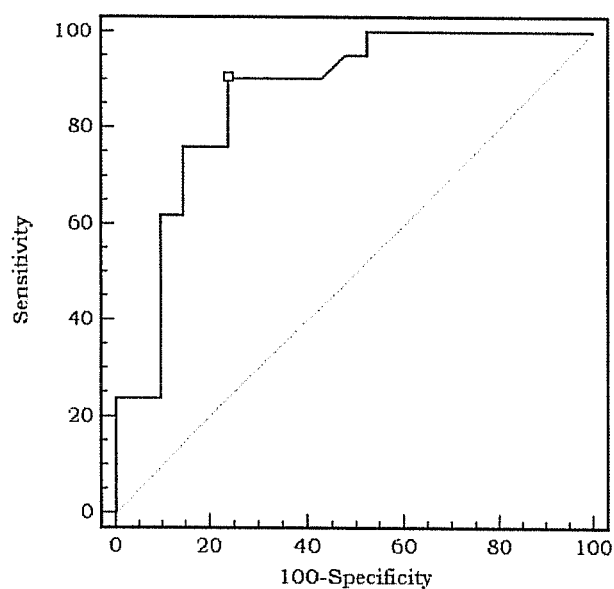
FIG. 31 depicts the ROC Analysis for Recombinant Fragment 3 IgG ELISA.

The raw IgG ELISA data for fragment 3 was analyzed with ROC curve determination using MedCalc statistical software. Performance analysis of ROC curve is shown in FIG. 31. AUC of recombinant virB10 is 0.863 (95% confidence interval; range: 0.721 to 0.949).

Experimental Protocol

*Anaplasma* IgG ELISA

1. Antigen coating concentration 0.5 µg/ml in carbonate buffer (pH 9.6) (100 µl per well). Coating overnight in 4° C.
2. Wash three time in PBST buffer (0.5% Tween-20)
3. Block with 200 µl blocker buffer (casein in PBS, Thermo Sci. #37528). Incubate for 1 hour in room temperature
4. Wash three times with PBST buffer (0.5% Tween-20)
5. Add 100 µl 1:200 diluted human sera (dilution buffer: 1:20 casein buffer in PBST). Incubate for 1 hour in room temperature
6. Wash four times with PBST buffer (0.5% Tween-20)
7. Add goat anti-human IgG antibody (1:15,000 diluted in casein dilution buffer (1:20 casein buffer in PBST). Incubate for 1 hour in room temperature
8. Wash four times with PBST buffer (0.5% Tween-20)
9. Add 100 µl TBM substrate. Incubate in room temperature for 3 minutes
10. Stop the reaction with 2N HCl
11. Read the result at $OD_{450}$

*Anaplasma* IgM ELISA

1. Antigen coating concentration 0.125 µg/ml in carbonate buffer (pH 9.6) (100 µl per well). Coating overnight in 4° C.
2. Wash three time in PBST buffer (0.5% Tween-20)
3. Block with 200 µl blocker buffer (casein in PBS, Thermo Sci. #37528). Incubate for 1 hour in room temperature
4. Wash three times with PBST buffer (0.5% Tween-20)
5. Dilute human sera in GullSorb™ (1:10) to prepare mixture 1. Incubate in room temperature for 5 minutes. Dilute incubated mixture 1 in sample dilution buffer (1:20 casein buffer in PBST). Therefore, the total dilution factor for human sera is 1:100
6. Add 100 µl 1:100 diluted human sera to the plate. Incubate for 1 hour in room temperature
7. Wash four times with PBST buffer (0.5% Tween-20)
8. Add goat anti-human IgM antibody (1:10,000 diluted in casein dilution buffer (1:20 casein buffer in PBST). Incubate for 1 hour in room temperature
9. Wash four times with PBST buffer (0.5% Tween-20)
10. Add 100 µl TBM substrate. Incubate in room temperature for 3 minutes
11. Stop the reaction with 2N HCl
12. Read the result at $OD_{450}$ All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Various modifications of the above-described modes for carrying out the invention that are obvious to those skilled in the filed of molecular biology, recombinant expression and related fields are intended to be within the scope of the following claims.

TABLE 1

Oligonucleotide Sequences Used in Gene Amplification for *Anaplasma phagocytophilum* Encoding Hemolysin and Non-Hemolysin Proteins

| Recombinant Protein | NCBI Accession # | Oligonucleotides | Gene Amplification |
|---|---|---|---|
| Hemolysin | YP_504658 | Fwd: 5'-gacgacgacaagatgggtgctggagtttttgaag-3' (SEQ ID No. 1) | Yes |

TABLE 1-continued

Oligonucleotide Sequences Used in Gene Amplification for *Anaplasma phagocytophilum* Encoding Hemolysin and Non-Hemolysin Proteins

| Recombinant Protein | NCBI Accession # | Oligonucleotides | Gene Amplification |
|---|---|---|---|
| | | Rev: 5'-gaggagaagcccggttcagcaagcagtattcctattcac-3' (SEQ ID No. 2) | |
| Succinate Dehydrogenase, iron-sulfur subunit | YP_504786 | Fwd: 5'-gacgacgacaagatggtgcagtttttctttgcc-3' (SEQ ID No. 3)<br>Rev: 5'-gaggagaagcccggtctagagctccaatccttttatc-3' (SEQ ID No. 4) | Yes |
| p44-8 Outer Membrane Protein | YP_504769 | Fwd: 5'-gacgacgacaagatgctaaggctcatggtgatgg-3' (SEQ ID No. 5)<br>Rev: 5'-gaggagaagcccggttcaaaaacgtattgtgcgacg-3' (SEQ ID No. 6) | Yes |

TABLE 2

Recombinant Expression of *Anaplasma phagocytophilum* Hemolysin and Non-Hemolysin Proteins

| Recombinant Hemolysin and Hemolysin Protein | NCBI Accession Nos. | Recombinant Expression |
|---|---|---|
| Hemolysin | YP_504658 (SEQ ID No. 7) | Yes |
| Succinate Dehydrogenase, iron-sulfur subunit | YP_504786 (SEQ ID No. 8) | No |
| P44-8 Outer Membrane Protein | YP_504769 (SEQ ID No. 9) | Yes |

TABLE 3

IgM/IgG ELISA Assays for Recombinant Hemolysin and p44

| Recombinant Proteins | IgM ELISA | IgG ELISA |
|---|---|---|
| Hemolysin | Sensitivity = 60.0%<br>Specificity = 92.9% | Sensitivity = 81.0%<br>Specificity = 57.1% |
| p44 Outer Membrane Protein | Sensitivity = 81%<br>Specificity = 90.5% | Sensitivity = 42%-71.4%<br>Specificity = 71.4%-100% |

TABLE 4

Primers for Generation of Polynucleotides Encoding Three (3) Recombinant Fragments of Hemolysin Protein of *Anaplasma phagocytophilum*

| Recombinant Hemolysin Fragments | Primers | Nucleotide Sequences |
|---|---|---|
| Fragment-1 | Forward | 5'-gacgacgacaagatgatgggtgctggagtttt-3' (SEQ ID No. 10) |
| | Reverse | 5'-gaggagaagcccggttagactcttgtatgttg-3' (SEQ ID No. 11) |
| Fragment-2 | Forward | 5'-gacgacgacaagatgagtgtccttaaaagcca-3' (SEQ ID No. 12) |
| | Reverse | 5'-gaggagaagcccggttagttttcgtattcgata-3' (SEQ ID No. 13) |
| Fragment-3 | Forward | 5'-gacgacgacaagatggatgagactgctattcc-3' (SEQ ID No. 14) |
| | Reverse | 5'-gaggagaagcccggttatcagcaagcagtatt-3' (SEQ ID No. 15) |

TABLE 5

ELISA Sensitivity and Specificity for Recombinant Hemolysin Protein Fragments

| Recombinant Fragments | IgG ELISA | IgM ELISA |
|---|---|---|
| Fragment 1 | Sensitivity = 90.5%<br>Specificity = 71.4% | Sensitivity = 85.7%<br>Specificity = 85.7% |
| Fragment 2 | Sensitivity = 90.5%<br>Specificity = 47.6% | Sensitivity = 84.6%<br>Specificity = 93.9% |
| Fragment 3 | Sensitivity = 90.5%<br>Specificity = 76.2% | Sensitivity = 81.0%<br>Specificity = 85.7% |

What is claimed is:

1. A composition comprising an isolated polypeptide and a support, wherein said isolated polypeptide is a recombinant polypeptide, consisting of the amino acid sequence selected from the group consisting of SEQ ID NO: 19, SEQ ID NO: 21, and SEQ ID NO: 23.

2. The composition of claim 1, wherein said isolated recombinant polypeptide consists of the amino acid sequence set forth in SEQ ID NO: 19.

3. The composition of claim 1, wherein said isolated recombinant polypeptide consists of the amino acid sequence set forth in SEQ ID NO: 21.

4. The composition of claim 1, wherein said isolated recombinant polypeptide consists of the amino acid sequence set forth in SEQ ID NO: 23.

5. The composition of claim 1, wherein said support is selected from the group consisting of polyethylene, polypropylene and glass.

6. The composition of claim 1, wherein said support is a microtiter well.

7. The composition of claim 2, wherein said isolated polypeptide is recombinantly expressed using an isolated polynucleotide, said isolated polynucleotide has a nucleotide sequence set forth in SEQ ID NO: 18.

8. The composition of claim 3, wherein said isolated polypeptide is recombinantly expressed using an isolated polynucleotide, said isolated polynucleotide has a nucleotide sequence set forth in SEQ ID NO: 20.

9. The composition of claim 4, wherein said isolated polypeptide is recombinantly expressed using an isolated polynucleotide, said isolated polynucleotide has a nucleotide sequence set forth in SEQ ID NO: 22.

10. A method of preparing the composition of claim 2, comprising the steps of:
   (i) introducing an isolated polynucleotide into a host cell, said isolated polynucleotide has a nucleotide sequence set forth in SEQ ID NO: 18;
   (ii) growing said host cell in a culture under suitable conditions to permit production of said isolated polypeptide;
   (iii) isolating said isolated polypeptide, and
   (iv) providing a support, wherein, said composition is comprised of said isolated polypeptide and said support.

11. A method of preparing the composition of claim 3, comprising the steps of:
   (i) introducing an isolated polynucleotide into a host cell, said isolated polynucleotide has a nucleotide sequence set forth SEQ ID NO: 20;
   (ii) growing said host cell in a culture under suitable conditions to permit production of said isolated polypeptide;
   (iii) isolating said isolated polypeptide, and
   (iv) providing a support, wherein, said composition is comprised of said isolated polypeptide and said support.

12. A method of preparing the composition of claim 4, comprising the steps of:
   (i) introducing an isolated polynucleotide into a host cell, said isolated polynucleotide has a nucleotide sequence set forth in SEQ ID NO: 22;
   (ii) growing said host cell in a culture under suitable conditions to permit production of said isolated polypeptide; and
   (iii) isolating said isolated polypeptide, and
   (iv) providing a support, wherein, said composition is comprised of said isolated polypeptide and said support.

13. The composition of claim 1, further comprising an isolated polypeptide and a support, wherein said isolated polypeptide is a recombinant polypeptide consisting of the amino acid sequence set forth in SEQ ID NO: 17.

14. The composition of claim 13, wherein said support is selected from the group consisting of polyethylene, polypropylene and glass.

15. The composition of claim 13, wherein said support is a microtiter well.

16. The composition of claim 13, wherein said isolated polypeptide set forth in SEQ ID NO: 17 is produced by a method comprising the steps of:
   (i) introducing an isolated polynucleotide into a host cell, said isolated polynucleotide has a nucleotide sequence set forth in SEQ ID NO: 16;
   (ii) growing said host cell in a culture under suitable conditions to permit production of said isolated polypeptide; and
   (iii) isolating said isolated polypeptide.

* * * * *